(12) United States Patent
Arnould

(10) Patent No.: US 7,317,010 B2
(45) Date of Patent: Jan. 8, 2008

(54) THIENO-PYRROLE COMPOUNDS AS ANTAGONISTS OF GONADOTROPIN RELEASING HORMONE

(75) Inventor: Jean Claude Arnould, Reims Cedex 2 (FR)

(73) Assignee: AstraZeneca AB, Sodertalje (SE)

( * ) Notice: Subject to any disclaimer, the term of this patent is extended or adjusted under 35 U.S.C. 154(b) by 482 days.

(21) Appl. No.: 10/525,109

(22) PCT Filed: Aug. 18, 2003

(86) PCT No.: PCT/GB03/03603

§ 371 (c)(1),
(2), (4) Date: Feb. 18, 2005

(87) PCT Pub. No.: WO2004/018479

PCT Pub. Date: Mar. 4, 2004

(65) Prior Publication Data

US 2006/0004053 A1    Jan. 5, 2006

(30) Foreign Application Priority Data

Aug. 21, 2002  (EP) ................... 02292076

(51) Int. Cl.
A61K 31/5377 (2006.01)
A61K 31/496 (2006.01)
C07D 413/02 (2006.01)

(52) U.S. Cl. .................. 514/235.8; 544/106; 544/111; 544/120; 544/121; 544/224; 544/336; 544/358; 544/360; 546/184; 546/193; 546/268.1; 546/276.4; 514/231.2; 514/247; 514/252.12; 514/336; 548/452; 548/453

(58) Field of Classification Search ........... 544/106, 544/111, 114, 120, 121, 224, 336, 358, 360; 546/184, 192, 193, 276.4; 514/235.8, 252.12, 514/336; 548/453
See application file for complete search history.

(56) References Cited

U.S. PATENT DOCUMENTS 6,025,366 A    2/2000   Walsh et al.
6,340,686 B1   1/2002   Furuya et al.

FOREIGN PATENT DOCUMENTS

| JP | 4179949 A | 6/1992 |
|---|---|---|
| JP | 4356029 A | 12/1992 |
| WO | WO 97/21435 A1 | 6/1997 |
| WO | WO 97/21703 A1 | 6/1997 |
| WO | WO 97/21704 A1 | 6/1997 |
| WO | WO 97/21707 A1 | 6/1997 |
| WO | WO 98/55116 A1 | 12/1998 |
| WO | WO 98/55119 A1 | 12/1998 |
| WO | WO 98/55123 A1 | 12/1998 |
| WO | WO 98/55470 A1 | 12/1998 |
| WO | WO 98/55479 A1 | 12/1998 |
| WO | WO 99/21553 A1 | 5/1999 |
| WO | WO 99/21557 A1 | 5/1999 |
| WO | 99/41251 | 8/1999 |
| WO | WO 99/41251 A1 | 8/1999 |
| WO | WO 99/41252 A1 | 8/1999 |
| WO | WO 99/51231 A1 | 10/1999 |
| WO | WO 99/51232 A1 | 10/1999 |
| WO | WO 99/51233 A1 | 10/1999 |
| WO | WO 99/51234 A1 | 10/1999 |
| WO | WO 99/51595 A1 | 10/1999 |
| WO | WO 99/51596 A1 | 10/1999 |
| WO | WO 00/04013 A1 | 1/2000 |
| WO | WO 00/53178 A1 | 8/2000 |
| WO | WO 00/53179 A1 | 8/2000 |
| WO | WO 00/53180 A1 | 8/2000 |
| WO | WO 00/53181 A1 | 8/2000 |
| WO | WO 00/53185 A1 | 8/2000 |
| WO | WO 00/53602 A1 | 8/2000 |
| WO | 00/53185 | 9/2000 |
| WO | WO 00/69433 A1 | 11/2000 |
| WO | 01/70227 | 9/2001 |
| WO | WO 01/70227 A1 | 9/2001 |
| WO | WO 02/66459 A1 | 8/2002 |
| WO | 02/92565 | 11/2002 |
| WO | WO 02/92565 A2 | 11/2002 |

OTHER PUBLICATIONS

Ashton et al. 'Substituted Indole-5-carboxamides and -acetamides as Potent Nonpeptide GnRH Receptor Antagonist.' Bioorganic & Medicinal Chemistry Letters 2001, vol. 11, pp. 1723-1726.

(Continued)

*Primary Examiner*—Golam M. M. Shameem

(57) ABSTRACT

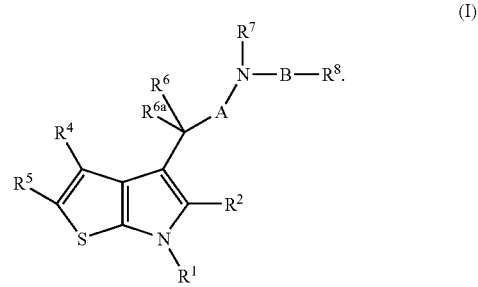

The invention relates to a group of novel thieno-pyrrole compounds of Formula (I), wherein: $R^1$, $R^2$, $R^4$, $R^5$, $R^6$, $R^{6a}$, $R^7$, $R^8$, A and B are as defined in the specification, which are useful as gonadotrophin releasing hormone antagonists. The invention also relates to pharmaceutical formulations of said compounds, methods of treatment using said compounds and to processes for the preparation of said compounds.

14 Claims, No Drawings

OTHER PUBLICATIONS

Ashton et al. 'Potent Nonpeptide GnHR Receptor Antagonists Derived from Substituted Indole-5-carboxamides and -acetamides Bearing a Pyridine Side-Chain Terminus.' Bioorganic & Medicinal Chemistry Letters 2001, vol. 11, pp. 1727-1731.

Ashton et al. 'Orally Bioavailable, Indole-Based Nonpeptide GnHR Receptor Antagonists with High Potency and Functional Activity.' Bioorganic and medicinal Chemistry Letters 2001, vol. 11, pp. 2597-2602.

Chu et al. 'Initial Structure-Activity Relationship of a Novel Class of Nonpeptidyl GnHR Receptor Antagonists: 2-Arylindoles.' Bioorganic and Medicinal Chemistry Letters 2001, vol. 11, pp. 509-513.

Chu et al. 'SAR Studies of novel 5-Substituted 2-Arylindoles as Nonpeptidyl GnHR Receptor Antagonists.' Bioorganic and Medicinal Chemistry Letters 2001, vol. 11, pp. 515-517.

Freidinger, R. M. 'Nonpeptide ligands for peptide and protein receptors.' Current Opinion in Chemical Biology 1999, vol. 3, pp. 395-406.

Goulet, M. T. 'Gonadotropin Releasing Hormone Antagonists.' Annual Reports in Medicinal Chemistry 1995, vol. 30, pp. 169-178.

Lin et al. '2-(3,5-Dimethylphenyl)tryptamine Derivatives That Bind to the GnHR Receptor.' Bioorganic & Medicinal Chemistry Letters 2001, vol. 11, pp. 1073-1076.

Lin et al. 'Heterocyclic Derivatives of 2-(3,5-Dimethylphenyl)tryptamine as GnHR Receptor Antagonists.' Bioorganic & Medicinal Chemistry Letters 2001, vol. 11, pp. 1077-1080.

Simoene, J. P. 'Synthesis of chiral β-methyl tryptamine-derived GnHR antagonists.' Tetrahedron Letters 2001, vol. 42, pp. 6459-6461.

Walsh et al. 'A convergent synthesis of (S)-β-methyl-2-aryltryptamine based gonadotropin releasing hormone antagonists.' Tetrahedron, 2001, vol. 57, pp. 5233-5241.

Young et al '2-Arylindoles as Gonadotropin Releasing Hormone (GnHR) Antagonists: Optimization of the Tryptamine Side Chain.' Bioorganic & Medicinal Chemistry Letters 2002, vol. 12, pp. 827-832.

Ujjainwalla, F. 'Total synthesis of 6- and 7-azaindole derived GnHR antagonists.' Tetrahedron Letters, 2001, vol. 42, pp. 6441-6445.

Simeone et al 'Modification of the Pyridine Moiety of Non-peptidyl Indole GnHR Receptor Antagonists.' Bioorganic & Medicinal Chemistry Letters, 2002, vol. 12, pp. 3329-3332.

Gibbs, J. B. 'Pharmaceutical Research in Molecular Oncology.' Cell, 1994, vol. 792, pp. 193-198.

Wensbo, D. 'Indoel-3-pyruvic acid Oxime ethers and Thieno analogues by Heck Cyclisation. Application to the Synthesis of Thia Tyrptophans' Tetrahedron, 1996, vol. 52(47), pp. 14975-14988.

Blair et al 'Thieno[3,2-b] and Thieno[2,3-b]pyrrole Bioisosteric Analogues of Hallucinogen and Serotonin Agonist N.N-Dimethyltryptamine' J. Med. Chem 1999, vol. 42, pp. 1106-1111.

Colburn et al 'Condensed Thiophen Ring Systems. Part 20. Synthesis of 5-Arylthieno-[3,2-b]pyrroles and 5-Arylthieno[3,2-c]pyrazoles' Journal of the Chemical Society Perkins I 1977, pp. 2436-2441.

Humphries et al 'The Synthesis of 6-Substituted Thieno[3,2-b]pyrroles. Analogs of Tryptophan, Tryptamine and Indoleacetic acid' The Journal of Organic Chemistry 1972, vol. 37, pp. 3626-3629.

Keener et al 'The Synthesis of 6-Substituted Thieno[3,2-b]pyrroles' The Journal of Organic Chemistry 1968, vol. 33(4), pp. 1355-1359.

Srinivasan et al 'A New Synthesis of 5-Arylthieno[2,3-b]pyrroles and 5-Arylthieno[3,2-b]pyrroles' Synthesis 1973, 313-315.

Synder et al 'Synthesis of the Thieno[3,2-b]pyrrole System' Journal of the American Chemical Society 1957, vol. 79, pp. 2556-2559.

Gale et al 'Preparation and Reactions of 5-Carbethoxythieno[3,2-b]pyrrole and Some of Its Derivatives' The Journal of Organic Chemistry 1964, vol. 29, pp. 2160-2165.

Aoyama, T. Chemical & Pharmaceutical Bulletin 1981 vol. 11, pp. 3249-3255.

Geetha et al' Indian Journal of Chemistry Section B 1979, vol. 17B(2), pp. 163-164.

Kumar et al' Indian Journal of Chemistry Section B 1979, vol. 18B(2), pp. 541-543.

Kvitko et al' Zhurnal Organicheskoi Khimii 1976, vol. 12(7), pp. 1574-1585 (+ Abstract).

Kvitko et al 'Enamines of formyl derivatives of thio- and selenopyrrolone and synthesis of thieno- an selenopheno[2,3-b]pyrroles' Khim Geterotsikl Soedin 1973, vol. (4), pp. 565-566 (+ Abstract).

THIENO-PYRROLE COMPOUNDS AS ANTAGONISTS OF GONADOTROPIN RELEASING HORMONE

CROSS-REFERENCE TO RELATED APPLICATIONS

This application is a U.S. National Stage under 35 U.S.C § 371 of International Application No. PCT/GB2003/003603, filed Aug. 18, 2003, which claims priority under 35 U.S.C. § 119(a)-(d) to European Patent Application No. 02292076.3 filed on Aug. 21, 2002, the specification of which is incorporated by reference herein.

The present invention relates to compounds which are antagonists of gonadotropin releasing hormone (GnRH) activity. The invention also relates to pharmaceutical formulations, the use of a compound of the present invention in the manufacture of a medicament, a method of therapeutic treatment using such a compound and processes for producing the compounds.

Gonadotropin releasing hormone (GnRH) is a decapeptide that is secreted by the hypothalamus into the hypophyseal portal circulation in response to neural and/or chemical stimuli, causing the biosynthesis and release of luteinizing hormone (LH) and follicle-stimulating hormone (FSH) by the pituitary. GnRH is also known by other names, including gonadoliberin, LH releasing hormone (LHRH), FSH releasing hormone (FSH RH) and LH/FSH releasing factor (LH/FSH RP).

GnRH plays an important role in regulating the action of LH and FSH (by regulation of their levels), and thus has a role in regulating the levels of gonadal steroids in both sexes, including the sex hormones progesterone, oestrogens and androgens. More discussion of GnRH can be found in WO 98/5519 and WO 97/14697, the disclosures of which are incorporated herein by reference.

It is believed that several diseases would benefit from the regulation of GnRH activity, in particular by antagonising such activity. These include sex hormone related conditions such as sex hormone dependent cancer, benign prostatic hypertrophy and myoma of the uterus. Examples of sex hormone dependent cancers are prostatic cancer, uterine cancer, breast cancer and pituitary gonadotrophe adenoma.

The following disclose compounds purported to act as GNRH antagonists: WO 97/21435, WO 97/21703, WO 97/21704, WO 97/21707, WO 55116, WO 98/55119, WO 98/55123, WO 98/55470, WO 98/55479, WO 99/21553, WO 99/21557, WO 99/41251, WO 99/41252, WO 00/04013, WO 00/69433, WO 99/51231, WO 99/51232, WO 99/51233, WO 99/51234, WO 99/51595, WO 99/51596, WO 00/53178, WO 00/53180, WO 00/53179, WO 00/53181, WO 00/53185, WO 00/53602, WO 02/066477, WO 02/666478, WO 02/06645 and WO 02/092565.

It would be desirable to provide further compounds, such compounds being GnRH antagonists. Thus, according to the first aspect of the invention there is provided a compound of Formula (I),

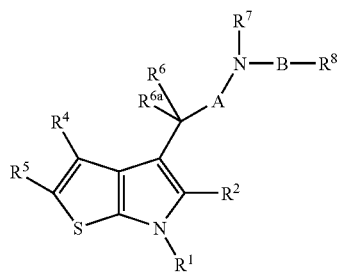

Formula (I)

wherein
A represents a direct bond or optionally substituted $C_{1-5}$alkylene;
B is a group of Formula (II):

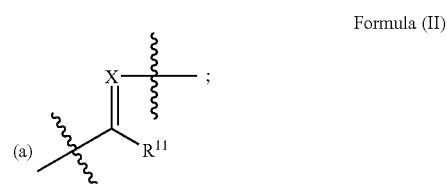

Formula (II)

wherein at position (a) Formula (II) is attached to the nitrogen atom and the group X is attached to $R^8$;

$R^1$ represents hydrogen; optionally substituted $C_{1-8}$alkyl; or $(CH_2)_b$—$R^a$, wherein $R^a$ represents $C_{3-8}$cycloalkyl and b is zero or an integer from 1 to 6;

$R^2$ represents an optionally substituted mono- or bi-cyclic aromatic ring structure wherein the optional substituents are selected from cyano, $NR^3R^{3a}$, optionally substituted $C_{1-8}$alkyl, optionally substituted $C_{1-8}$alkoxy or halo;

$R^3$ and $R^{3a}$ are independently selected from hydrogen; optionally substituted $C_{1-8}$alkyl and optionally substituted aryl;

$R^4$ is hydrogen;

$R^5$ is selected from an optionally substituted 3- to 8-membered heterocyclic ring containing from 1 to 4 heteroatoms independently selected from O, N and S; or a group of formula III-a; III-b; III-c; III-d; III-e; III-f, III-g, III-h, III-i, III-j, III-k or III-l;

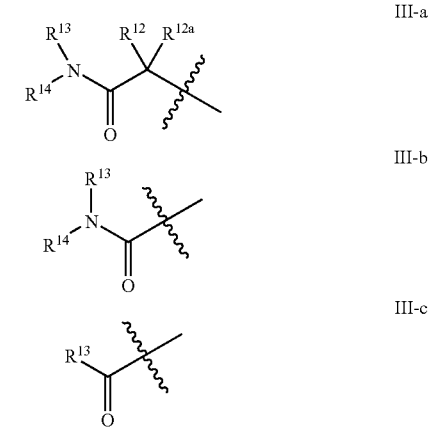

-continued

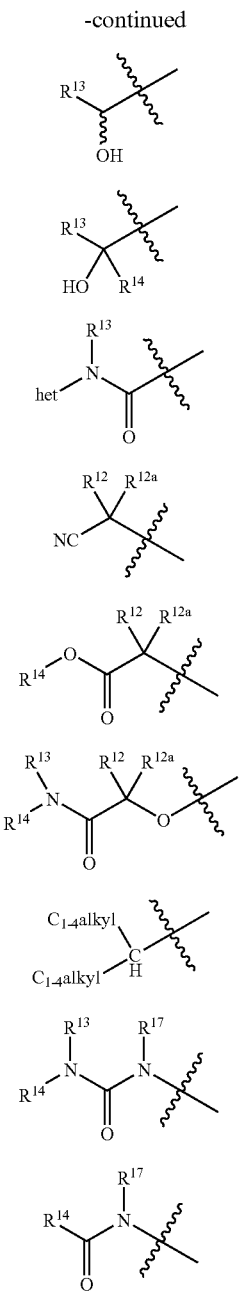

III-d

III-e

III-f

III-g

III-h

III-i

III-j

III-k

III-l wherein het represents an optionally substituted 3- to 8-membered heterocyclic ring containing from 1 to 4 heteroatoms independently selected from O, N and S;

$R^6$ and $R^{6a}$, are independently selected from hydrogen and optionally substituted $C_{1-8}$alkyl; or $R^6$ and $R^{6a}$ together represent carbonyl;

$R^7$ represents hydrogen or optionally substituted $C_{1-8}$alkyl; or

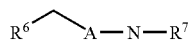

together form an optionally substituted 3- to 8-membered heterocyclic ring containing from 1 to 3 further heteroatoms independently selected from O, N and S, and $R^{6a}$ represents hydrogen and optionally substituted $C_{1-8}$alkyl;

X and $R^8$ are selected from:
(i) X represents N and $R^8$ is selected from:
    cyano, hydrogen, hydroxy, —O—$R^b$, —C(O)—$R^b$, —NR$^b$R$^c$—C(O)O—$R^b$, —CONR$^b$R$^c$ or NH—C(O)—$R^b$, where $R^b$ and $R^c$ are independently selected from hydrogen and $C_{1-4}$alkyl optionally substituted with hydroxy, amino, N—$C_{1-4}$alkylamino, N,N-di-$C_{1-4}$alkylamino, HO—$C_{2-4}$alkyl-NH— or HO—$C_{2-4}$alkyl-N($C_{1-4}$alkyl)-;
(ii) X represents CH and $R^8$ represents NO$_2$; and
(iii) =X—$R^8$ together represent =O;

$R^{11}$ is a group of the formula: N($R^9R^{10}$) wherein $R^9$ represents hydrogen, optionally substituted aryl, an optionally substituted 3- to 10 membered heterocyclic ring or optionally-substituted $C_{1-8}$alkyl and $R^{10}$ represents hydrogen or optionally substituted $C_{1-8}$alkyl; or the structure N($R^9R^{10}$) represents an optionally-substituted 3- to 10 membered heterocyclic ring optionally containing from 1 to 3 further heteroatoms independently selected from O, N and S;

$R^{12}$ and $R^{12a}$ are independently selected from hydrogen or optionally substituted $C_{1-8}$alkyl; or $R^{12}$ and $R^{12a}$ together with the carbon to which they are attached form an optionally substituted 3 to 7-membered cycloalkyl ring;

$R^{13}$ and $R^{14}$ are selected from:
(i) $R^{13}$ is selected from hydrogen; optionally substituted $C_{1-8}$alkyl; optionally substituted aryl; —$R^d$—Ar, where $R^d$ represents $C_{1-8}$alkylene and Ar represents optionally substituted aryl; and optionally substituted 3- to 8-membered heterocyclic ring optionally containing from 1 to 3 further heteroatoms independently selected from O, N and S; and $R^{14}$ is selected from hydrogen; optionally substituted $C_{1-8}$alkyl and optionally substituted aryl;
(ii) where $R^5$ represents a group of formula III-a, III-b, III-i or III-k, then the group NR$^{13}$(—$R^{14}$) represents an optionally substituted 3- to 8-membered heterocyclic ring optionally containing from 1 to 3 further heteroatoms independently selected from O, N and S; or
(iii) where $R^5$ represents structure III-e, then the group

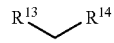

represents an optionally substituted 3- to 8-membered heterocyclic ring optionally containing from 1 to 4 heteroatoms independently selected from O, N and S;

$R^{17}$ is selected from: hydrogen and $C_{1-4}$alkyl;

or a salt, pro-drug or solvate thereof.

According to a further feature of the first aspect of the invention there is provided a compound of Formula (Ia),

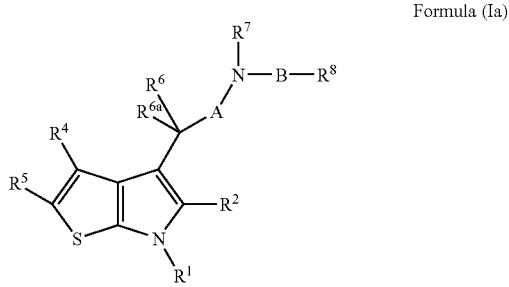

Formula (Ia)

wherein

A represents a direct bond or optionally substituted $C_{1-5}$alkylene;

B is a group of Formula (II):

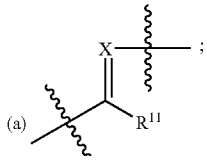

Formula (II)

wherein at position (a) Formula (II) is attached to the nitrogen atom and the group X is attached to $R^8$;

$R^1$ represents hydrogen; optionally substituted $C_{1-8}$alkyl; or $(CH_2)_b$—$R^a$, wherein $R^a$ represents $C_{3-8}$cycloalkyl and b is zero or an integer from 1 to 6;

$R^2$ represents an optionally substituted mono- or bi-cyclic aromatic ring structure wherein the optional substituents are selected from cyano, $NR^3R^{3a}$, optionally substituted $C_{1-8}$alkyl, optionally substituted $C_{1-8}$alkoxy or halo;

$R^3$ and $R^{3a}$ are independently selected from hydrogen; optionally substituted $C_{1-8}$alkyl and optionally substituted aryl;

$R^4$ is hydrogen;

$R^5$ is selected from an optionally substituted 3- to 8-membered heterocyclic ring containing from 1 to 4 heteroatoms independently selected from O, N and S; or a group of formula III-a; III-b; III-c; III-d; III-e; III-f, III-g, III-h, III-i or: III-j;

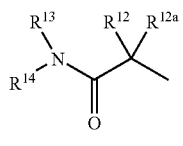
III-a

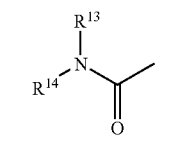
III-b

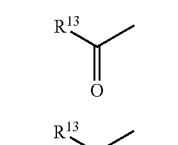
III-c

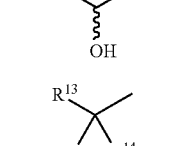
III-d

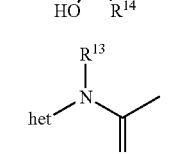
III-e

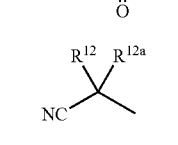
III-f

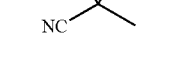
III-g

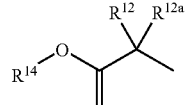
III-h

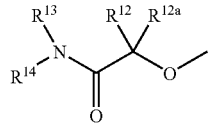
III-i

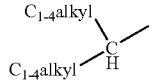
III-j wherein het represents an optionally substituted 3- to 8-membered heterocyclic ring containing from 1 to 4 heteroatoms independently selected from O, N and S;

$R^6$ and $R^{6a}$, are independently selected from hydrogen and optionally substituted $C_{1-8}$alkyl; or $R^6$ and $R^{6a}$ together represent carbonyl;

$R^7$ represents hydrogen or optionally substituted $C_{1-8}$alkyl; or

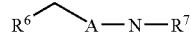

together form an optionally substituted 3- to 8-membered heterocyclic ring containing from 1 to 3 further heteroatoms independently selected from O, N and S, and $R^{6a}$ represents hydrogen and optionally substituted $C_{1-8}$alkyl;

X and $R^8$ are selected from:
  (i) X represents N and $R^8$ is selected from:
    cyano, hydrogen, hydroxy, —O—$R^b$, —$NR^bR^c$—C(O) O—$R^b$, —$CONR^bR^c$ or NH—C(O)—$R^b$, where $R^b$ and $R^c$ are independently selected from hydrogen and $C_{1-4}$alkyl optionally substituted with hydroxy, amino, N—$C_{1-4}$alkylamino, N,N-di-$C_{1-4}$alkylamino, HO—$C_{2-4}$alkyl-NH— or HO—$C_{2-4}$alkyl-N($C_{1-4}$alkyl)-;
  (ii) X represents CH and $R^8$ represents $NO_2$; and
  (iii) X—$R^8$ together represent —O—;

$R^{11}$ is a group of the formula: $N(R^9R^{10})$ wherein $R^9$ represents hydrogen, aryl, an optionally substituted 3- to 10 membered heterocyclic ring or optionally-substituted $C_{1-8}$alkyl and $R^{10}$ represents hydrogen or optionally substituted $C_{1-8}$alkyl; or the structure $N(R^9R^{10})$ represents an optionally-substituted 3- to 10 membered heterocyclic ring optionally containing from 1 to 3 further heteroatoms independently selected from O, N and S;

$R^{12}$ and $R^{12a}$ are independently selected from hydrogen or optionally substituted $C_{1-8}$alkyl; or $R^{12}$ and $R^{12a}$ together with the carbon to which they are attached form an optionally substituted 3 to 7-membered cycloalkyl ring;

$R^{13}$ and $R^{14}$ are selected from:
  (i) $R^{13}$ is selected from hydrogen; optionally substituted $C_{1-8}$alkyl; optionally substituted aryl; —$R^d$—Ar, where $R^d$ represents $C_{1-8}$alkylene and Ar represents optionally substituted aryl; and optionally substituted 3- to 8-membered heterocyclic ring optionally containing from 1 to 3 further heteroatoms independently selected from O, N and S; and $R^{14}$ is selected from hydrogen; optionally substituted $C_{1-8}$alkyl and optionally substituted aryl;

(ii) where $R^5$ represents a group of formula III-a, III-b or III-i, then the group $NR^{13}(—R^{14})$ represents an optionally substituted 3- to 8-membered heterocyclic ring optionally containing from 1 to 3 further heteroatoms independently selected from O, N and S; or (iii) where $R^5$ represents structure III-e, then the group

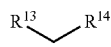

represents an optionally substituted 3- to 8-membered heterocyclic ring optionally containing from 1 to 4 heteroatoms independently selected from O, N and S;

or a salt, pro-drug or solvate thereof.

According to a further feature of the first aspect of the invention there is provided a pharmaceutical formulation comprising a compound of Formula (I) or Formula (Ia), or salt, pro-drug or solvate thereof, and a pharmaceutically acceptable diluent or carrier.

According to a further feature of the first aspect of the invention there is provided the following uses of a compound of a compound of Formula (I) or Formula (Ia), or salt, pro-drug or solvate thereof:

(a) the use in the manufacture of a medicament for antagonising gonadotropin releasing hormone activity;

(b) the use in the manufacture of a medicament for administration to a patient, for reducing the secretion of luteinizing hormone by the pituitary gland of the patient; and (c) the use in the manufacture of a medicament for administration to a patient, for therapeutically treating and/or preventing a sex hormone related condition in the patient, preferably a sex hormone related condition selected from prostate cancer and pre-menopausal breast cancer.

According to a further aspect of the invention there is provided a method of antagonising gonadotropin releasing hormone activity in a patient, comprising administering a compound of Formula (I) or Formula (Ia), or salt, prodrug or solvate thereof, to a patient.

Whilst pharmaceutically-acceptable salts of compounds of the invention are preferred, other non-pharmaceutically-acceptable salts of compounds of the invention may also be useful, for example in the preparation of pharmaceutically-acceptable salts of compounds of the invention.

Whilst the invention comprises compounds of the invention, and salts, pro-drugs or solvates thereof, in a further embodiment of the invention, the invention comprises compounds of the invention and salts thereof.

In the present specification, unless otherwise indicated, an alkyl, alkylene or alkenyl moiety may be linear or branched.

The term "alkylene" refers to the group —$CH_2$—. Thus, $C_8$ alkylene for example is —$(CH_2)_8$—.

The term "aryl" refers to phenyl or naphthyl.

The term "carbamoyl" refers to the group —$CONH_2$.

The term "halo" refers to fluoro, chloro, bromo or iodo.

The term "heterocyclyl" or "heterocyclic ring" refers to a 4-12 membered, preferably 5-10 membered aromatic mono or bicyclic ring or a 4-12 membered, preferably 5-10 membered saturated or partially saturated mono or bicyclic ring, said aromatic, saturated or partially unsaturated rings containing up to 5 heteroatoms independently selected from nitrogen, oxygen or sulphur, linked via ring carbon atoms or ring nitrogen atoms where a bond from a nitrogen is allowed, for example no bond is possible to the nitrogen of a pyridine ring, but a bond is possible through the 1-nitrogen of a pyrazole ring. Examples of 5- or 6-membered aromatic heterocyclic rings include pyrrolyl, furanyl, imidazolyl, triazolyl, pyrazinyl, pyrimidinyl, pyridazinyl, pyridinyl, isoxazolyl, oxazolyl, 1,2,4 oxadiazolyl, isothiazolyl, thiazolyl and thienyl. A 9 or 10 membered bicyclic aromatic heterocyclic ring is an aromatic bicyclic ring system comprising a 6-membered ring fused to either a 5 membered ring or another 6 membered ring. Examples of 5/6 and 6/6 bicyclic ring systems include benzofuranyl, benzimidazolyl, benzthiophenyl, benzthiazolyl, benzisothiazolyl, benzoxazolyl, benzisoxazolyl, indolyl, pyridoimidazolyl, pyrimidoimidazolyl, quinolinyl, isoquinolinyl, quinoxalinyl, quinazolinyl, phthalazinyl, cinnolinyl and naphthyridinyl. Examples of saturated or partially saturated heterocyclic rings include pyrrolinyl, pyrrolidinyl, morpholinyl, piperidinyl, piperazinyl, dihydropyridinyl and dihydropyrimidinyl. This definition further comprises sulphur-containing rings wherein the sulphur atom has been oxidised to an S(O) or S(O2) group.

The term "aromatic ring" refers to a 5-10 membered aromatic mono or bicyclic ring optionally containing up to 5 heteroatoms independently selected from nitrogen, oxygen or sulphur. Examples of such "aromatic rings" include: phenyl, pyrrolyl, furanyl, imidazolyl, triazolyl, pyrazinyl, pyriminyl, pyridazinyl, pyridinyl, isoxazolyl, oxazolyl, 1,2,4 oxadiazolyl, isothiazolyl, thiazolyl and thienyl. Preferred aromatic rings include 'phenyl, thienyl and pyridyl.

The symbol

denotes where the respective group is linked to the remainder of the molecule.

For the avoidance of doubt, when

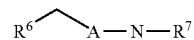

together form an optionally substituted 3- to 8-membered heterocyclic ring containing from 1 to 3 further heteroatoms independently selected from O, N and S, then the groups shown cyclise to form a nitrogen-containing heterocyclic ring, i.e

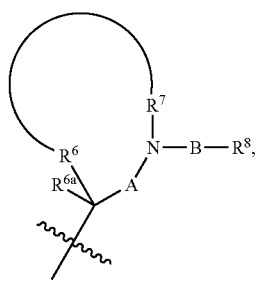

optionally containing from 1 to 3 further heteroatoms independently selected from O, N and S.

Examples of $C_{1-8}$alkyl include: methyl, ethyl, propyl, isopropyl, butyl, iso-butyl, tert-butyl and 2-methyl-pentyl; example of $C_{1-8}$alkylene include: methylene, ethylene and 2-methyl-propylene; examples of $C_{1-8}$alkoxy include methoxy, ethoxy and butyloxy; examples of N—$C_{1-4}$alkylamino include N-methylamino and N-ethylamino; examples of N,N-di-$C_{1-4}$alkylamino, examples of HO—$C_{2-4}$alkyl-NH include hydroxymethylamino hydroxyethylamino and hydroxypropyamino, examples of HO—C$_{2-4}$alkyl-N(C$_{1-4}$ alkyl) include N-methyl-hydroxymethylamino, N-ethyl-hydroxyethylamino, and N-propyl-hydroxypropyamino.

It is to be understood that, insofar as certain of the compounds of the invention may exist in optically active or racemic forms by virtue of one or more asymmetric carbon atoms, the invention includes in its definition any such optically active or racemic form which possesses the property of antagonizing gonadotropin releasing hormone (GnRH) activity. The synthesis of optically active forms may be carried out by standard techniques of organic chemistry well known in the art, for example by synthesis from optically active starting materials or by resolution of a racemic form. Similarly, activity of these compounds may be evaluated using the standard laboratory techniques referred to hereinafter.

The invention also relates to any and all tautomeric forms of the compounds of the different features of the invention that possess the property of antagonizing gonadotropin releasing hormone (GnRH) activity.

It will also be understood that certain compounds of the present invention may exist in solvated, for example hydrated, as well as unsolvated forms. It is to be understood that the present invention encompasses all such solvated forms which possess the property of antagonizing gonadotropin releasing hormone (GnRH) activity.

Preferred compounds of Formula (I) are those wherein any one of the following or a combination of the following apply.

Preferably A represents optionally substituted C$_{1-5}$alkylene. Further preferably C$_{1-4}$alkylene. Most preferably methylene or ethylene.

Preferably R$^1$ represents hydrogen or optionally substituted C$_{1-6}$alkyl. More preferably R$^1$ represents hydrogen or unsubstituted C$_{1-6}$alkyl. Yet more preferably R$^1$ represents hydrogen, methyl, ethyl or tert-butyl. Most preferably R$^1$ represents hydrogen.

Preferably R$^2$ represents an optionally substituted monocyclic aromatic ring structure wherein the optional substituents are selected from cyano, NR$^e$R$^f$, optionally substituted C$_{1-8}$alkyl (preferably, C$_{1-4}$alkyl, eg, methyl or ethyl), optionally substituted C$_{1-8}$alkoxy (preferably, C$_{1-6}$alkoxy, eg, methoxy, ethoxy or tert-butoxy) or halo (eg, F, Br or Cl) wherein R$^e$ and R$^f$ are independently selected from hydrogen, C$_{1-6}$alkyl or aryl. Further preferably R$^2$ is optionally substituted phenyl wherein the optional substituents are selected from cyano, NR$^e$R$^f$, optionally substituted C$_{1-4}$alkyl, optionally substituted C$_{1-6}$alkoxy, F, Br or Cl wherein R$^e$ and R$^f$ are as defined above. Yet further preferably R$^2$ is optionally substituted phenyl wherein the optional substituents are selected from methyl, ethyl, methoxy, ethoxy, tert-butoxy, F or Cl. Most preferably R$^2$ represents

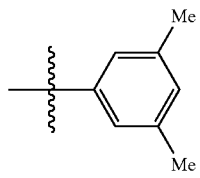

wherein Me represents methyl. Preferably R$^2$ bears 1, 2 or 3 substituents.

Preferably R$^3$ and R$^{3a}$ are independently selected from hydrogen; optionally substituted C$_{1-6}$alkyl and, optionally substituted aryl. Further preferably R$^3$ and R$^{3a}$ are independently selected from methyl, ethyl, tert-butyl and phenyl.

Preferably R$^5$ is selected from a group of formula III-a, III-g, III-h, III-i or III-j:

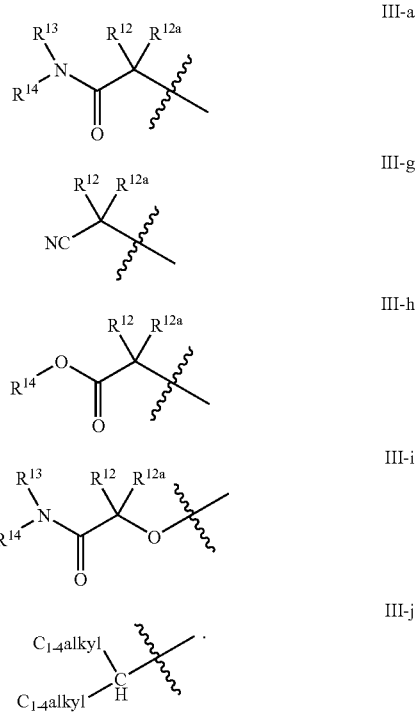

Further preferably R$^5$ is selected from one of the following groups:

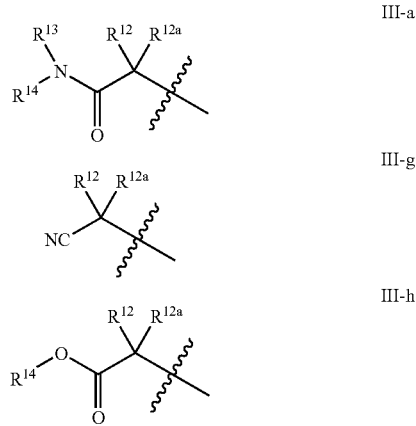

Yet further preferably R$^5$ is selected from one of the following groups:

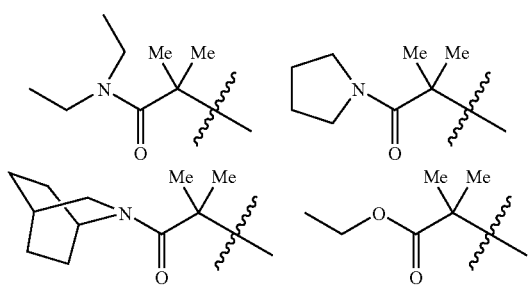

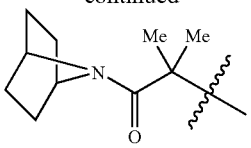

wherein Me represents methyl.

Yet further preferably $R^5$ is selected from one of the following groups:

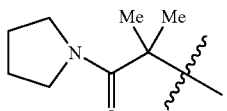 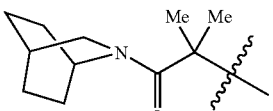

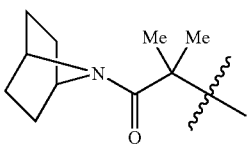

Most preferably $R^5$ is:

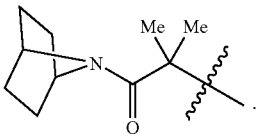

Preferably $R^6$ and $R^{6a}$ are independently selected from hydrogen, fluoro or optionally substituted $C_{1-6}$alkyl. Preferably $R^6$ and $R^{6a}$ are independently selected from hydrogen, fluoro and unsubstituted $C_{1-6}$alkyl. Yet more preferably $R^6$ and $R^{6a}$ are independently selected from hydrogen or methyl. Most preferably $R^6$ is hydrogen and $R^{6a}$ is methyl.

In a further embodiment of the invention, $R^6$ and $R^{6a}$ each represent hydrogen and A represents $C_{1-4}$alkylene (preferably methylene).

In a yet further embodiment of the invention $R^6$ represents hydrogen, $R^{6a}$ represents methyl, and A represents $C_{1-4}$alkylene (preferably methylene).

Preferably $R^7$ is selected from hydrogen or optionally-substituted $C_{1-6}$alkyl. Further preferably $R^7$ represents hydrogen, methyl, ethyl or tert-butyl). Most preferably $R^7$ is hydrogen.

Preferably X and $R^8$ are selected from:
(a) =X—$R^8$ represents =O; or
(b) X represents N and $R^8$ represents hydrogen, hydroxy, cyano, —O—$R^b$, —C(O)—$R^b$, —C(O)O—$R^b$ and —C(O)N$R^b R^c$; wherein $R^b$ and $R^c$ are as defined above.

Further preferably X and $R^8$ represent either:
(a) X represents N and $R^8$ represents cyano or —C(O)O—$R^b$; or
(b) X represents N and $R^8$ represents hydrogen.

Further preferably X and $R^8$ represent either:
(a) X represents N and $R^8$ represents cyano or —C(O)O—$R^b$; wherein $R^b$ represents $C_{1-6}$alkyl;

In a further embodiment of the invention X represents N and $R^8$ represents —CON$R^b R^c$ wherein $R^b$ and $R^c$ are as defined above.

In a further embodiment of the invention the group =X—$R^8$ is selected from:

(a) X represents N and $R^8$ represents hydrogen, cyano, hydroxy, —O—$R^b$, —C(O)—$R^b$, and —C(O)O—$R^b$, wherein $R^b$ is selected from methyl, ethyl or isopropyl;
(b) X represents N and $R^8$ represents carbamoyl; and
(c) =X—$R^e$ represents =O.

In a further embodiment of the invention the group =X—$R^8$ is selected from:
(a) X represents N and $R^8$ represents hydrogen, cyano, hydroxy, carbamoyl, acetyl, methoxy, methoxycarbonyl, ethoxycarbonyl or isopropoxycarbonyl; and
(b) =X—$R^8$ represents =O. In a further embodiment of the invention the group =X—$R^8$ is selected from:
(a) X represents N and $R^8$ represents methoxycarbonyl, ethoxycarbonyl or isopropoxycarbonyl; and
(b) =X—$R^8$ represents =O.

Preferably $R^9$ comprises part of the optionally substituted heterocyclic ring $N(R^9 R^{10})$ or is hydrogen, optionally substituted aryl, an optionally substituted 3- to 10 membered heterocyclic ring or optionally substituted $C_{1-6}$alkyl, preferably $C_{1-4}$alkyl, wherein the optional substituents are selected from: hydroxy, amino, nitro, cyano, optionally-substituted aryl, optionally substituted 3- to 8-membered heterocyclyl containing from 1 to 4 heteroatoms independently selected from O, N and S, —O—$R^b$, C(O)N$R^b R^c$, —N$R^b R^c$, —N$R^c$C(O)—$R^b$, —C(O)N$R^b R^c$, —N$R^c$S(O$_{0-2}$)$R^b$, —S(O$_{0-2}$)$R^b$, wherein $R^b$ and $R^c$ are as defined above.

Further preferably $R^9$ comprise part of the optionally substituted heterocyclic ring $N(R^9 R^{10})$ or is selected from optionally substituted $C_{1-6}$alkyl.

Yet further preferably $R^9$ comprise part of the optionally substituted heterocyclic ring $N(R^9 R^{10})$ or is selected from optionally subsituted $C_{1-6}$alkyl, wherein the optional subsitutents are selected from: cyano or an optionally substituted 3 to 10 membered heterocyclic ring.

Yet further preferably $R^9$ comprise part of the optionally substituted heterocyclic ring $N(R^9 R^{10})$.

When $R^9$ is a $C_{1-6}$alkyl group substituted by an optionally-substituted 3 to 10 membered heterocyclic ring containing from 1 to 4 heteroatoms independently selected from O, N and S, the heterocyclic ring is preferably selected from pyridyl, thienyl, piperidinyl, imidazolyl, triazolyl, thiazolyl, pyrrolidinyl, piperazinyl, morpholinyl, imidazolinyl, benztriazolyl, benzimidazolyl, pyrimidinyl, pyrazinyl, pyridazinyl, oxazolyl, furanyl, pyrrolyl, 1,3-dioxolanyl, 2-azetinyl, each of which is optionally substituted, wherein the optional substituents are preferably selected from $R^{16}$. Further preferably a group of formula VI-a, VI-b, VI-c, VI-d, VI-e, VI-f, VI-g, VI-h, VI-i, VI-j or VI-k:, wherein each group is optionally substituted by one or more groups selected from $R^{16}$.

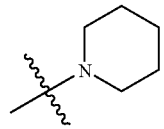

VI-a

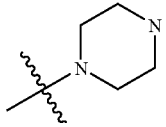

VI-b

-continued

VI-c

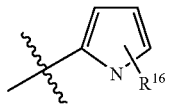

VI-j

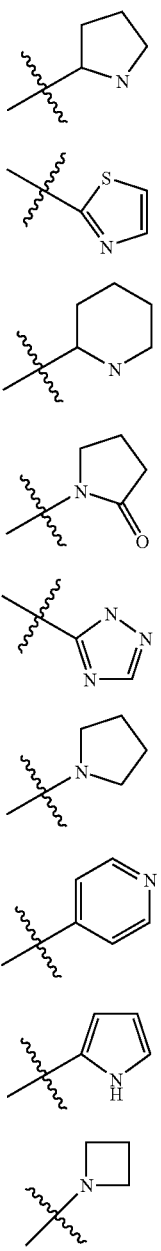

wherein
R[16] represents hydrogen, aryl, a 3- to 10 membered heterocyclic ring or optionally substituted $C_{1-4}$alkyl wherein the optional substituents are selected from: hydroxy, amino, nitro, cyano, optionally-substituted phenyl, optionally substituted 3- to 8-membered heterocyclyl containing from 1 to 4 heteroatoms independently selected from O, N and S, —O—$R^b$, C(O)NR$^b$R$^c$, —NR$^b$R$^c$, —NR$^c$C(O)—R$^b$, —C(O)NR$^b$R$^c$, —NR$^c$S(O$_{0-2}$)R$^b$, —S(O$_{0-2}$)R$^b$, wherein R$^b$ and R$^c$ are as defined above; Preferably R[16] represents hydrogen or $C_{1-4}$alkyl optionally substituted by hydroxy, amino, nitro or cyano. Most preferably R[16] represents hydrogen or methyl.

Most preferably when R[9] is a $C_{1-6}$alkyl group substituted by an optionally-substituted 3 to 10 membered heterocyclic ring containing from 1 to 4 heteroatoms independently selected from O, N and S, the heterocyclic ring is preferably selected piperazinyl, pyridyl or pyrrolyl, optionally substituted with methyl.

When R[9] is a $C_{1-6}$alkyl group substituted by an optionally-substituted 3 to 10 membered heterocyclic ring containing from 1 to 4 heteroatoms independently selected from O, N and S, the $C_{1-6}$alkyl group is preferably selected from ethyl or propyl.

Preferably R[10] comprises part of the group N(R[9]R[10]) or is optionally substituted $C_{1-6}$alkyl. Further preferably R[10] comprises part of the group N(R[9]R[10]) or is selected from: methyl, ethyl or tert-butyl. Most preferably R[10] comprises part of the group N(R[9]R[10]).

When N(R[9]R[10]) represent an optionally substituted 3- to 10-membered heterocyclic ring, N(R[9]R[10]) is preferably selected from a 5- or 6-membered monocyclic ring containing between 1 and 3 (preferably 1 or 2) heteroatom independently selected from O, N and S. Further preferably a 5- or 6-membered monocyclic ring containing between 1 and 3 (preferably 1 or 2) heteroatom independently selected from O, N and S selected from pyrrolidinyl, thienyl, pyrazolidinyl, piperidinyl, morpholinyl, thiomorpholinyl piperazinyl, imidazole, or azetidinyl. Further preferably the structure N(R[9]R[10]) is a heterocyclic ring selected from an optionally-substituted group of formula, IV-a, IV-b, IV-c, IV-d and IV-e, wherein the optional substituents are preferably selected from the groups listed for R[15] below Further preferably a group of formula VI-b, VI-i, or VI-j:

VI-b

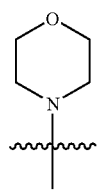

VI-i

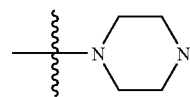

IV-a

IV-b

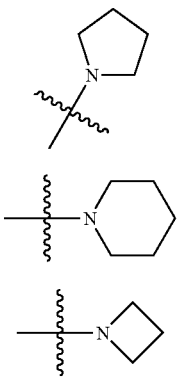

IV-c

IV-d

IV-e

Further preferably the structure N(R$^9$R$^{10}$) is selected from a group of formula Va, Vb or Vc:

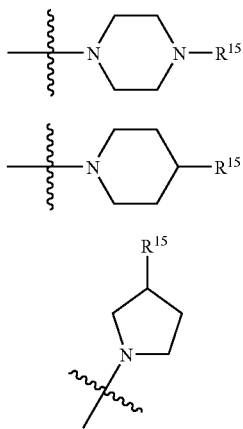

V-a

V-b

V-c

Most preferably the structure N(R$^9$R$^{10}$) is a group of formula V-a or V-c:

R$^{15}$ represents the group R$^{15a}$-Z- wherein:

R$^{15a}$ represents hydrogen, optionally substituted aryl, an optionally substituted 3- to 10 membered heterocyclic ring or optionally substituted C$_{1-4}$alkyl, wherein the optional substituents are selected from: hydroxy, amino, nitro, cyano, optionally-substituted aryl, optionally substituted 3- to 8-membered heterocyclyl containing from 1 to 4 heteroatoms independently selected from O, N and S, —O—R$^g$, —C(O)—R$^g$, —C(O)NR$^g$R$^h$, —NR$^g$R$^h$, —NR$^h$C(O)—R$^g$, —C(O)NR$^g$R$^h$, —NR$^h$S(O$_{0-2}$)R$^g$, —S(O$_{0-2}$)R$^g$, wherein R$^g$ and R$^g$ are independently selected from: heterocyclyl, hydrogen and C$_{1-4}$alkyl optionally substituted with hydroxy, amino, N—C$_{1-4}$alylamino, N,N-di-C$_{1-4}$alkylamino, HO—C$_{2-4}$alkyl-NH— or HO—C$_{2-4}$alkyl-N(C$_{1-4}$alkyl)-. Preferably R$^{15}$ is heterocyclyl, —C(O)-heterocyclyl or —(CH$_2$)$_{0-2}$—C(O)NR$^g$R$^h$, wherein R$^g$ and R$^h$ are independently selected from C$_{1-4}$alkyl or hydrogen; and Z is selected from: a direct bond, —(CH$_2$)$_{s1}$—, —(CH$_2$)$_{s1}$—O—(CH$_2$)$_{s2}$—, —(CH$_2$)$_{s1}$—C(O)—(CH$_2$)$_{s2}$—, —(CH$_2$)$_{s1}$—S(O$_n$)—(CH$_2$)$_{s2}$—, —(CH$_2$)$_{s1}$—N(R$^{18}$)—(CH$_2$)$_{s2}$—, —(CH$_2$)$_{s1}$—C(O)N(R$^{18}$)— (CH$_2$)$_{s2}$—, —(CH$_2$)$_{s1}$—N(R$^{18}$)C(O)—(CH$_2$)$_{s2}$, —(CH$_2$)$_{s1}$—N(R$^{18}$)C(O)N(R$^{18}$)—(CH$_2$)$_{s2}$—, —(CH$_2$)$_{s1}$—OC(O)—(CH$_2$)$_{s2}$—, —(CH$_2$)$_{s1}$—C(O)O—(CH$_2$)$_{s2}$—, —(CH$_2$)$_{s1}$—N(R$^{18}$)C(O)O—(CH$_2$)$_{s2}$—, —(CH$_2$)$_{s1}$—OC(O)N(R$^{18}$)—(CH$_2$)$_{s2}$—, —(CH$_2$)$_{s1}$—OS(O$_n$)—(CH$_2$)$_{s2}$—, or —(CH$_2$)$_{s1}$—S(O$_n$)—O—(CH$_2$)$_{s2}$—, —(CH$_2$)$_{s1}$—S(O)$_2$N(R$^{18}$)—(CH$_2$)$_{s2}$—, —(CH$_2$)$_{s1}$—N(R$^{18}$)S(O)$_2$—(CH$_2$)$_{s2}$—; wherein the —(CH$_2$)$_{s1}$— and —(CH$_2$)$_{s2}$— groups are independently optionally substituted by hydroxy or C$_{1-4}$alkyl and s1 and s2 are independently an integer from 0 to 2, wherein s1+s2 is less than or equal to 2 and R$^{18}$ is selected from hydrogen or C$_{1-4}$alkyl (preferably hydrogen).

Preferred values for Z are selected from: —(CH$_2$)$_{s1}$—, —(CH$_2$)$_{s1}$—O—(CH$_2$)$_{s2}$—, —(CH$_2$)$_{s1}$—C(O)—, —C(O)—(CH$_2$)$_{s2}$—, —(CH$_2$)$_{s1}$—N(R$^{18}$)—, —(CH$_2$)$_{s1}$—C(O)N(R$^{18}$)—, —(CH$_2$)$_{s1}$—NR$^{18}$)C(O)—(CH$_2$)$_{s2}$—, —(CH$_2$)$_{s1}$—S(O)$_2$—N(R$^{18}$)— or —(CH$_2$)$_{s1}$—NHS(O)$_2$—, wherein s1 and s2 are independently selected from 0,1, or 2 and s1+s2 is less than or equal to 2, R$^{18}$ is selected from hydrogen or C$_{1-4}$alkyl (preferably hydrogen) and the —(CH$_2$)$_s$— group is optionally substituted by hydroxy or C$_{1-4}$alkyl.

Further preferred values for Z are selected from: a direct bond, methylene, ethylene, propylene, oxy, 2-hydroxypropylene, carbonyl, methylcarbonyl, ethylcarbonyl, (methyl)methylcarbonyl, (ethyl)methylcarbonyl, carbonylmethylene, carbonylethylene, ethoxyethylene, amino, 2-hydroxypropylamino, carbonylamino, methylcarbonylamino, aminocarbonyl, methylaminocarbonyl, methylaminocarbonylmethyl, propylsulphonylamino or methylaminosulphonyl The most preferred values for Z are a direct bond or carbonyl.

Further preferably R$^{15}$ is selected from: N-isopropylaminocarbonylmethyl, tetrahydropyranyl, morpholinocarbonyl, pyridyl, pyrazinyl, pyridazinyl, pyrimidinyl or thiazolyl.

Yet further preferably R$^{15}$ is N-isopropylaminocarbonylmethyl, tetrahydropyranyl, morpholinocarbonyl or pyridyl.

Most preferably R$^{15}$ is pyridyl.

In a further embodiment of the invention R$^{15}$ represents hydrogen, optionally substituted aryl, an optionally substituted 3- to 10 membered heterocyclic ring or optionally substituted C$_{1-4}$alkyl wherein the optional substituents on aryl, a heterocyclic ring or C$_{1-4}$alkyl are selected from: hydroxy, amino, nitro, cyano, optionally-substituted aryl, optionally substituted 3- to 8-membered heterocyclyl containing from 1 to 4 heteroatoms independently selected from O, N and S, —O—R$^b$, C(O)NR$^b$R$^c$, —NR$^b$R$^c$, —NR$^c$C(O)—R$^b$, —C(O)NR$^b$R$^c$, —NR$^c$S(O$_{0-2}$)R$^b$, —S(O$_{0-2}$)R$^b$, wherein R$^b$ and R$^c$ are as defined above. Preferably R$^{15}$ is heterocyclyl. Further preferably R$^{15}$ is selected from: pyridyl, pyrazinyl, pyridazinyl, tetrahydropyranyl, pyrimidinyl or thiazolyl. Most preferably R$^{15}$ is pyridyl.

In a further embodiment of the invention N(R$^9$R$^{10}$) represent an optionally substituted 3- to 10-membered heterocyclic ring, wherein the optional substituents are selected from R$^{15}$ as defined above.

Preferably R$^{12}$ and R$^{12a}$ are independently selected from: hydrogen, optionally substituted C$_{1-6}$alkyl or R$^{12}$ and R$^{12a}$ together with carbon to which they are attached from an optionally substituted 3- to 6-membered cycloalkyl ring. Further preferably R$^{12}$ and R$^{12a}$ are independently selected from: hydrogen, methyl, ethyl or tert-butyl. Most preferably R$^{12}$ and R$^{12a}$ are both methyl.

Preferably R$^{13}$ and R$^{14}$, are independently selected from hydrogen, optionally substituted C$_{1-6}$alkyl, optionally substituted phenyl and —R$^d$-phenyl, where R$^d$ represents C$_{1-6}$alkylene or and an optionally substituted 3- to 8-membered heterocyclic ring (preferably, a 5- or 6-membered monocyclic ring) containing from 1 to 3 (preferably 1 or 2) further heteroatoms independently selected from O, N and S. Further preferably R$^{13}$ and R$^{14}$, are independently selected from hydrogen or C$_{1-6}$alkyl.

Where optional substitution is mentioned at various places, this refers to one, two, three or more optional substituents. Unless otherwise indicated above (ie, where a list of optional substituents is provided), each substituent can be independently selected from C$_{1-8}$alkyl (eg, C$_{2-6}$alkyl, and most preferably methyl, ethyl or tert-butyl); C$_{3-8}$cycloalkoxy, preferably cyclopropoxy, cyclobutoxy or cyclopentoxy; C$_{1-6}$alkoxy, preferably methoxy or C$_{2-4}$alkoxy; halo, preferably Cl or F; Hal$_3$C—, Hal$_2$CH—, HalCH$_2$—, Hal$_3$CO—, Hal$_2$CHO or Hal CH$_2$O, wherein Hal represents halo (preferably F); R$^g$CH$_2$O—, R$^h$C(O)N(R)—, R$^h$SO$_2$N(R)— or R$^g$—R$^h$N—, wherein R$^g$ and R$^h$ independently represent hydrogen or C$_{1-8}$alkyl (preferably methyl or C$_{2-6}$alkyl or C$_{2-4}$alkyl), or R$^g$—R$^h$N— represents an optionally substituted C$_{3-8}$, preferably C$_{3-6}$, heterocyclic ring optionally containing from 1 to 3 further heteroatoms independently selected from O, N and S; hydrogen; or R$^k$C(O)O— or R$^k$C(O)—, R$^k$ representing hydrogen, optionally substituted phenyl or C$_{1-6}$alkyl (preferably methyl, ethyl, iso-propyl or tert-butyl). For optional substitution of the heterocyclic ring represented by R$^g$—R$^h$N—, at least one (eg, one, two or three) substituents may be provided independently selected from C$_{1-6}$alkyl (eg, C$_{2-4}$alkyl, more preferably methyl); phenyl; CF$_3$O—; F$_2$CHO—; C$_{1-8}$alkoxy, preferably methoxy, ethoxy or C$_{3-6}$alkoxy; C$_{1-8}$alkoxyC(O), preferably methoxycarbonyl, ethoxycarbonyl, tert-butoxycarbonyl or C$_{3-6}$alkoxyC(O)—; phenoxycarbonyl; phenoxy; C$_{1-8}$alkanoyl, preferably acetyl, ethanoyl or C$_{3-6}$alkyanoyl; carboxy; C$_{1-8}$alkylS(O)$_{nn}$ wherein nn is an integer between 0 and 2, preferably methylthio, ethylthio, C$_{3-6}$alkylthio, methylsulphinyl, ethylsulphinyl, C$_{3-6}$alkylsulphinyl, methylsulphonyl, ethylsulphonyl or C$_{3-6}$akylsulphonyl; hydroxy; halo (eg, F, Cl or Br); R$'''$R$''$N— where R$'''$ and R$''$ are independently hydrogen or C$_{1-6}$alkyl (preferably C$_{2-4}$alkyl, more preferably methyl, most preferably R$'''$=R$''$=methyl); and nitro.

Where optional substitution of a ring is mentioned at various places, this most preferably refers to one, two, three or more substituents selected from C$_{1-8}$alkyl (eg, C$_{2-6}$alkyl, and most preferably methyl); C$_{1-8}$alkoxy, preferably methoxy, ethoxy or C$_{3-6}$alkoxy; C$_{1-8}$alkylS(O)$_{nn}$ wherein nn is an integer between 0 and 2, preferably methylthio, ethylthio, C$_{3-6}$alkylthio, methylsulphinyl, ethylsulphinyl, C$_{3-6}$alkylsulphinyl, methylsulphonyl, ethylsulphonyl or C$_{3-6}$alkylsulphonyl; halo (eg, F, Cl or Br); cyano; and NO$_2$.

A preferred group of compounds of the invention comprise compounds of Formula (I) wherein:

R$^{11}$ is a group of the formula: N($^9$R$^{10}$); and

N(R$^9$R$^{10}$) represents an optionally-substituted 3- to 8-membered heterocyclic ring optionally containing from 1 to 3 further heteroatoms independently selected from O, N and S, preferably substituted by heterocyclyl;

or a salt, pro-drug or solvate thereof.

A preferred group of compounds of the invention comprise compounds of Formula (I) wherein:

R$^{11}$ is a group of the formula: N(R$^9$R$^{10}$);

R$^9$ is a C$_{1-6}$alkyl group substituted by an optionally-substituted 3 to 8 membered heterocyclic ring containing from 1 to 4 heteroatoms independently selected from O, N and S; and R$^{10}$ represents hydrogen or C$_{1-6}$alkyl or a salt, pro-drug or solvate thereof.

A preferred group of compounds of the invention comprises a compound of Formula (Ib):

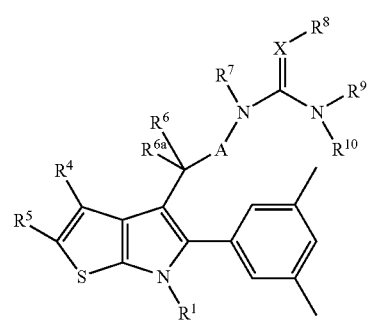

Formula (Ib)

wherein:

A, B, X, R$^1$, R$^2$, R$^3$, R$^{3a}$, R$^4$, R$^6$, R$^{6a}$, R$^7$, R$^8$, R$^9$, R$^{10}$, R$^{11}$, R$^{12}$ and R$^{12a}$ are as defined above;

or a salt, pro-drug or solvate thereof.

A preferred group of compounds of the invention comprises a compound of Formula (Ic):

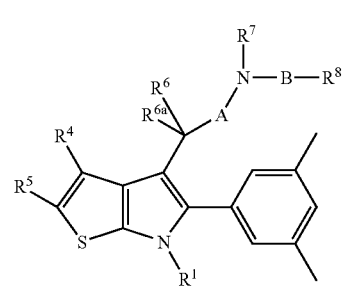

Formula (Ic)

wherein:

R$^5$ is selected from a IIIa, IIIb, IIIg, IIIi or IIIj:

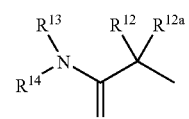

III-a

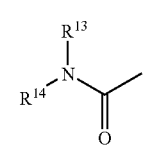

III-b

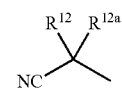

III-g

-continued

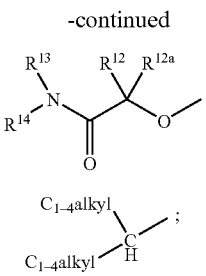

III-i

III-j and A, B, X, $R^1$, $R^3$, $R^{3a}$, $R^4$, $R^6$, $R^{6a}$, $R^7$, $R^8$, $R^9$, $R^{10}$, $R^{11}$, $R^{12}$, $R^{12a}$, $R^{13}$, and $R^{14}$ are as defined above;

or a salt, pro-drug or solvate thereof.

A further preferred group of compounds of the invention comprises a compound of Formula (Id):

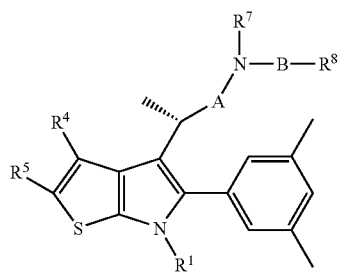

Formula (Id)

wherein:
$R^5$ is selected from a IIIa, IIIb, IIIg, IIIi or IIIj:

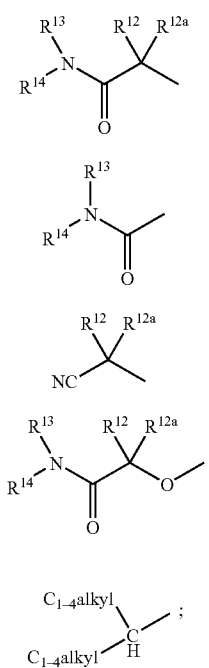

III-a

III-b

III-g

III-i

III-j and A, B, X, $R^1$, $R^2$, $R^3$, $R^{3a}$, $R^4$, $R^5$, $R^6$, $R^{6a}$, $R^7$, $R^8$, $R^9$, $R^{10}$, $R^{11}$, $R^{12}$, $R^{12a}$, $R^{13}$, and $R^{14}$ are as defined above;

or a salt, pro-drug or solvate thereof.

A yet further preferred group of compounds of the invention comprises a compound of Formula (Ib), (Ic) or (Id) wherein:
$R^5$ is a group of formula IIIa:

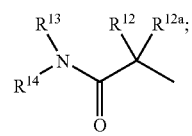

IIIa $NR^{13}(-R^{14})$ represents an optionally substituted 7- to 8-membered bicyclic heterocyclic ring and A, B, X, $R^1$, $R^2$, $R^3$, $R^{3a}$, $R^4$, $R^6$, $R^{6a}$, $R^7$, $R^8$, $R^9$, $R^{10}$, $R^{11}$, $R^{12}$ and $R^{12a}$ are as defined above;

or a salt, pro-drug or solvate thereof.

Particularly preferred compounds according to the present invention are wherein the compound is selected from:

2-(1,1-dimethyl-2-oxo-2-azabicyclo[2.2.1]heptan-7-yl-ethyl)-4-[1S-methyl-2-(N'-isopropoxycarbonyl-3-pyrid-4-yl-pyrrolidin-1-ylcarboximidamido)ethyl]-5-(3,5-dimethylphenyl)-6H-thieno[2,3-b]pyrrole;

2-(1,1-dimethyl-2-oxo-2-azabicyclo[2.2.1]heptan-7-yl-ethyl)-4-[2-(N'-isopropoxycarbonyl-3-pyrid-4-yl-pyrrolidin-1-ylcarboximidamido)ethyl]-5-(3,5-dimethylphenyl)-6H-thieno[2,3-b]pyrrole;

2-(2-pyrrolidin-1-yl-1,1-dimethyl-2-oxoethyl)-4-[1S-methyl-2-(N'-isopropoxycarbonyl-3-pyrid-4-yl-pyrrolidin-1-ylcarboximidamido)ethyl]-5-(3,5-dimethylphenyl)-6H-thieno[2,3-b]pyrrole;

2-(1,1-dimethyl-2-oxo-2-azabicyclo[2.2.1]heptan-7-yl-ethyl)-4-[1S-methyl-2-(N'-isopropoxycarbonyl-4-tetrahydropyran-4-yl-piperidin-1-ylcarboximidamido)ethyl]-5-(3,5-dimethylphenyl)-6H-thieno[2,3-]pyrrole;

2-(1,1-dimethyl-2-oxo-2-azabicyclo[2.2.1]heptan-7-yl-ethyl)-4-[1S-methyl-2-(3-pyrid-4-yl-pyrrolidin-1-ylcarbonyl)ethyl]-5-(3,5-dimethylphenyl)-6H-thieno[2,3-b]pyrrole;

2-(1,1-dimethyl-2-oxo-2-azabicyclo[2.2.1]heptan-7-yl-ethyl)-4-[1S-methyl-2-(N'-ethoxycarbonyl-3-pyrid-4-yl-pyrrolidin-1-ylcarboximidamido)ethyl]-5-(3,5-dimethylphenyl)-6H-thieno[2,3-b]pyrrole;

or a salt, pro-drug or solvate thereof.

In another embodiment of the invention particularly preferred compounds are wherein the compound is selected from:

isopropyl(1E)({(2R)-2-[2-[2-(7-azabicyclo[2.2.1]hept-7-yl)-1,1-dimethyl-2-oxoethyl]-5-(3,5-dimethylphenyl)-6H-thieno[2,3-b]pyrrol-4-yl]propyl}amino)(3-pyridin-4-ylpyrrolidin-1-yl)methylidinecarbamate;

isopropyl(1E)-({2-[2-[2-(7-azabicyclo[2.2.1]hept-7-yl)-1,1-dimethyl-2-oxoethyl]-5-(3,5-(3,5-dimethylphenyl)-6H-thieno[2,3-b]pyrrol-4-yl]ethyl}amino)(3-pyridin-4-ylpyrrolidin-1-yl)methylidenecarbamate;

isopropyl(1E)({(2R)-2-[2-[2-pyrrolidin-1-yl-1,1-dimethyl-2-oxoethyl]-5-(3,5-dimethylphenyl)-6H-thieno[2,3-b]pyrrol-4-yl]propyl}amino)(3-pyridin-4-ylpyrrolidin-1-yl)methylidinecarbamate;

methyl(1E)({(2R)-2-[2-[2-pyrrolidin-1-yl-1,1-dimethyl-2-oxoethyl]-5-(3,5-dimethylphenyl)-6H-thieno[2,3-b]pyrrol-4-yl]propyl}amino)(3-pyridin-4-ylpyrrolidin-1-yl)methylidinecarbamate;

isopropyl(1E)({(2R)-2-[2-[N,N-dimethylamino-1,1-dimethyl-2-oxoethyl]-5-(3,5-dimethylphenyl)-6H-thieno[2,3-b]pyrrol4-yl]propyl}amino)(3-pyridin-4-ylpyrrolidin-1-yl)methylidinecarbamate;

isopropyl(1E)({(2R)-2-[2-[1,1dimethyl-1-cyano-methyl]-5-(3,5-dimethylphenyl)-6H-thieno[2,3-b]pyrrol-4-yl]propyl}amino)(3-pyridin-4-ylpyrrolidin-1-yl)methylidinecarbamate;

isopropyl(1E)({(2R)-2-[2-[ethoxycarbonyl-1,1-dimethylmethyl]-5-(3,5-dimethylphenyl)-6H-thieno[2,3-b]pyrrol-4-yl]propyl}amino)(3-pyridin-4-ylpyrrolidin-1-yl)methylidinecarbamate;

isopropyl(1E)({(2R)-2-[2-[aminocarbonyl-1,1-dimethylmethyl]-5-(3,5-dimethylphenyl)-6H-thieno[2,3-b]pyrrol-4-yl]propyl}amino)(3-pyridin-4-ylpyrrolidin-1-yl)methylidinecarbamate; and N-{(2R)-2-[2-(1,1-dimethyl-2-oxo-2-pyrrolidin-1-ylethyl)-6H-thieno[2,3-b]pyrrol-4-yl]propyl}-3-pyridin-4-ylpyrrolidine-1-carboxamide;

or a salt, pro-drug or solvate thereof.

According to a further feature of the first aspect of the invention there is provided a pharmaceutical formulation comprising a compound of Formula (Ib), Formula (Ic), Formula (Id) or preferred compounds of the invention, or salt, pro-drug or solvate thereof, and a pharmaceutically acceptable diluent or carrier.

According to a further feature of the first aspect of the invention there is provided the following uses of a compound of a compound of Formula (Ib), Formula (Ic), Formula (Id) or preferred compounds of the invention, or salt, pro-drug or solvate thereof:

(a) the use in the manufacture of a medicament for antagonising gonadotropin releasing hormone activity;
(b) the use in the manufacture of a medicament for administration to a patient, for reducing the secretion of luteinizing hormone by the pituitary gland of the patient; and
(c) the use in the manufacture of a medicament for administration to a patient, for therapeutically treating and/or preventing a sex hormone related condition in the patient, preferably a sex hormone related condition selected from prostate cancer and pre-menopausal breast cancer.

The compounds of Formula (I) may be administered in the form of a pro-drug which is broken down in the human or animal body to give a compound of the Formula (I). Examples of pro-drugs include in-vivo hydrolysable esters of a compound of the Formula (I). Various forms of pro-drugs are known in the art. For examples of such prodrug derivatives, see:

a) Design of Prodrugs, edited by H. Bundgaard, (Elsevier, 1985) and Methods in Enzymology, Vol. 42, p. 309-396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113-191 (1991);
c) H. Bundgaard, Advanced Drug Delivery Reviews, 8, 1-38 (1992);
d) R Bundgaard, et al., Journal of Pharmaceutical Sciences, 77,285 (1988); and
e) N. Kakeya, et al., Chem Pharm Bull, 32, 692 (1984).

An in-vivo hydrolysable ester of a compound of the Formula (I) containing a carboxy or a hydroxy group is, for example, a pharmaceutically-acceptable ester which is hydrolysed in the human or animal body to produce the parent acid or alcohol. Suitable pharmaceutically-acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxyC$_{1-6}$alkyl esters for example 1-cyclohexylcarbonyloxyethyl; 1,3-dioxolen-2-onylmethyl esters, for example 5-methyl-1,3-dioxolen-2-onylmethyl; and $C_{1-6}$alkoxycarbonyloxyethyl esters.

An in-vivo hydrolysable ester of a compound of the Formula (1) containing a hydroxy group includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxy-methoxy. A selection of in-vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

The compounds of Formula (I) can be prepared by a process comprising a step selected from (a) to (f) as follows, these processes are provided as a further feature of the invention:

(a) Reaction of a compound of formula XXXII as follows

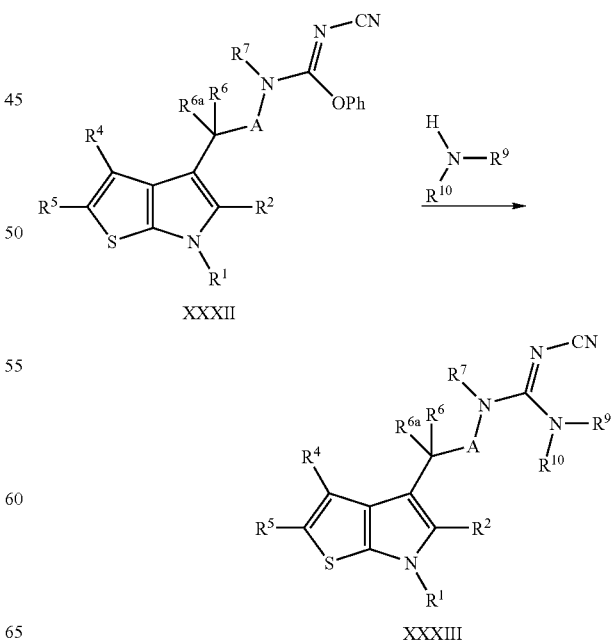

(b) Cleavage of the cyano group of compound of formula XXXIII in the presence of acid to produce compound of formula XXXIV

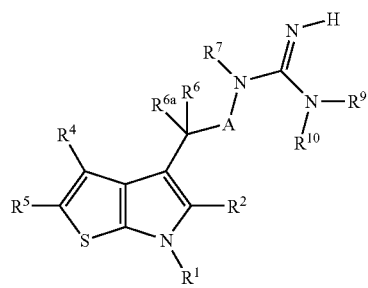

XXXIV (c) Reaction of compound of formula XXXV as follows

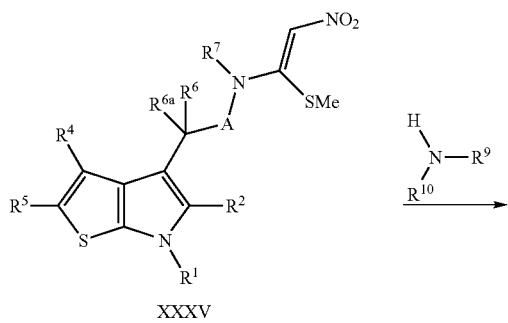

XXXV

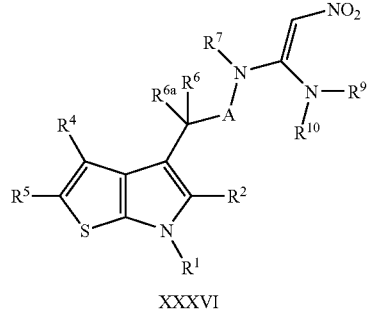

XXXVI (d) Reaction of compound of formula XXXVII as follows

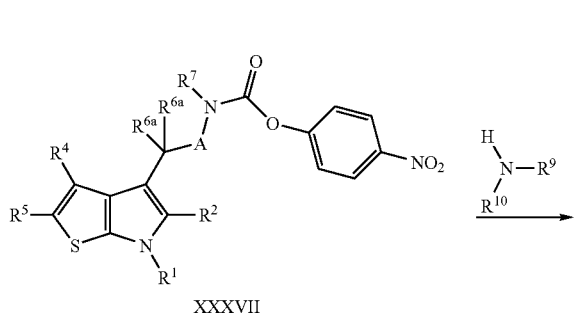

XXXVII

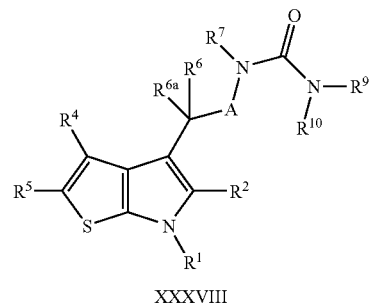

XXXVIII (e) Reaction of compound of formula XXXIX as follows

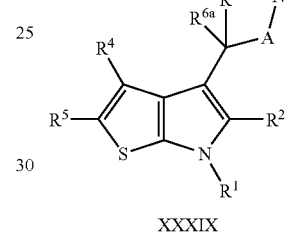

XXXIX

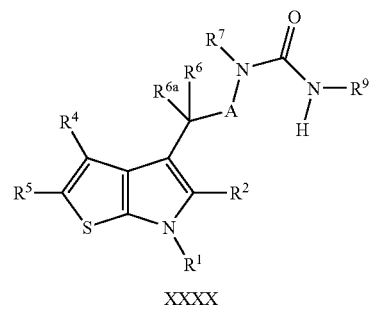

XXXX (f) to form a compound wherein X is nitrogen and Reaction of a compound of formula XXXXI as follows

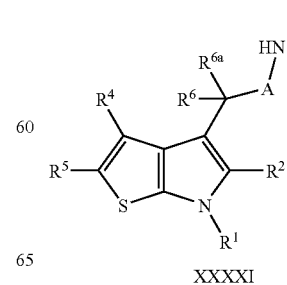

XXXXI

-continued

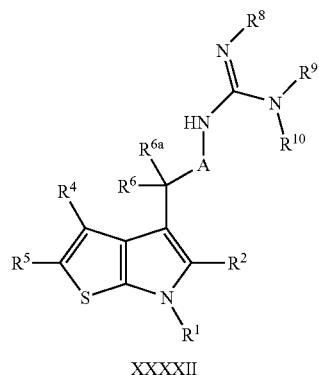

XXXXII and thereafter if necessary:
i) converting a compound of the Formula (I) into another compound of the Formula (I);
ii) removing any protecting groups;
iii) forming a salt, pro-drug or solvate.

It will be appreciated by the processes of the present invention certain functional groups such as hydroxyl or amino groups in the starting reagents or intermediate compounds may need to be protected by protecting groups. Thus, the preparation of the compounds of Formula (I) may involve, at an appropriate stage, the addition and subsequent removal of one or more protecting groups.

The protection and de-protection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The de-protection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The de-protection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium-on-carbon.

EXPERIMENTAL

General Reaction Schemes

In the following schemes wherein Ri, Rii and Riii represent optional substituents on the phenyl ring which are optionally protected as necessary and R represents a protecting group, group C has been depicted as substituted phenyl for illustration purposes only. Other definitions of C are also appropriate.

Thienopyrroles, such as 3 can be synthesised by the classic Fisher thienopyrrole synthesis reaction by the condensation of a hydrazine-HCl 1 and a ketone 2, bearing hydrogen atoms α to the carbonyl (Scheme a). Treatment of these reactants in a suitable solvent, such as acetic acid, ethanol, sec-butanol, toluene, in the presence of an acid, such as sulphuric, hydrochloric, polyphosphoric and/or a Lewis acid, for example, boron trifluoride, zinc chloride, magnesium bromide, at elevated temperatures (for example 100° C.), gives the desired product. R represents a protecting group, eg tert-butylcarbamate or phthalimide.

Scheme b

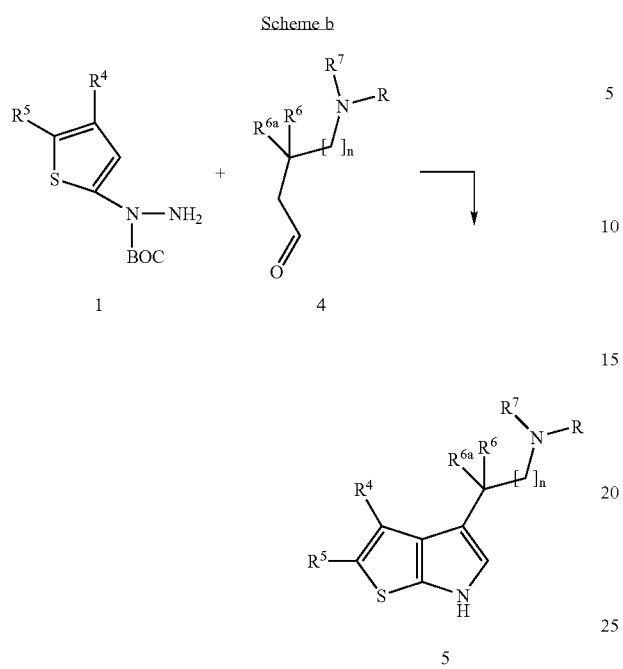

Thienopyrroles, such as represented in structure 5, can also be made using aldehydes 4, bearing hydrogen atoms α to the carbonyl, by cyclization using the conditions above. In this case the substituent at the 2-position must be added later (see scheme d).

Scheme c

Thienopyrrole may also be synthesised utilising the Granburg reaction, wherein a hydrazine 1 is mixed with ketone 6, bearing a chlorine atom γ to the carbonyl, and heated in a suitable solvent such as ethanol, sec-butanol, toluene at a temperature between 50° C. and 120° C. (Scheme c).

Scheme d

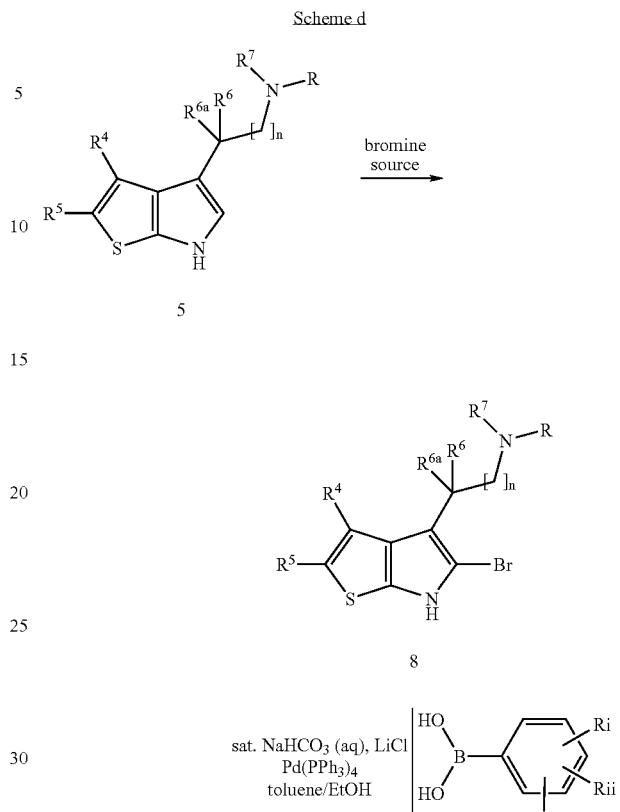

The thienopyrrole 5 can be treated with a 'bromine source', such as molecular bromide, pyridinium tribromide, pyrrolidone hydrobromide or polymer supported reagent equivalents, in an inert solvent such as chloroform, methylene chloride at −10° C. to 25° C. to yield the 2-bromo compound 8 (Scheme d). Reaction under Suzuki conditions with a palladium(0) catalyst, a weak base such aqueous sodium carbonate or saturated sodium hydrogen carbonate and the like, and a substituted aryl boronic acid from commercial sources or prepared (as described in: Gronowitz, S.; Hornfeldt, A.-B.; Yang, Y.,-H *Chem. Sci.* 1986, 26, 311-314), in an inert solvent such as toluene, benzene, dioxane, TBF, DMF and the like, with heating between 25° C. and 100° C., preferably 80° C., for a period of 1-12 hours, to give the desired compound 3.

3.

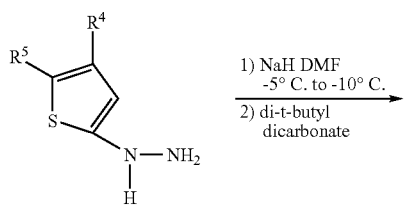

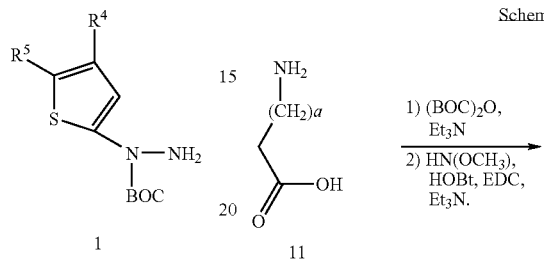

The thiophene 1 can be synthesised by reaction of a hydrazine under the preferred conditions of sodium hydride in DMF at a temperature between −10° C. and −5° C., followed by reaction with di-tert-butyldicarbonate in Th under reflux.

Scheme e.

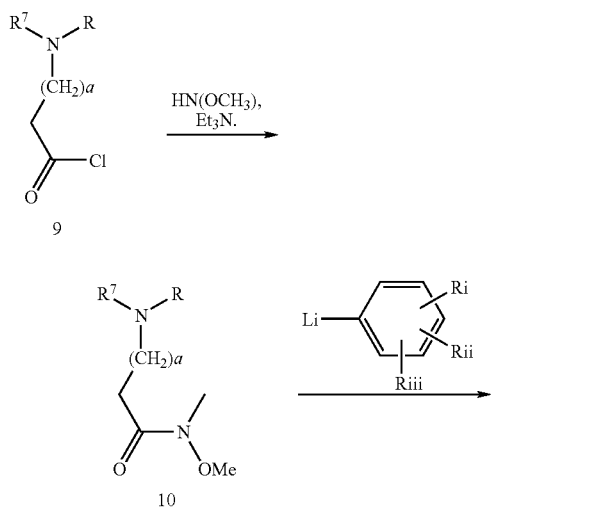

Substituted ketones 2 can be prepared, as outlined in Scheme e starting from appropriate acid chlorides such as 9. Treatment of the acid chloride with N,N-dimethylhydroxylamine hydrochloride in the presence of an amine base such as triethylamine, and a suitable solvent such as methylene chloride at a temperature of −10° C. to 25° C., yields the amide 10. Further reaction with a substituted aryl organo-lithium (prepared essentially as described in Wakefield B, J.; *Organolithium Methods* Academic Press Limited, 1988, pp. 27-29 and references therein) in an inert solvent such as tetrahydrofuran, diethyl ether, benzene, toluene or mixture thereof and the like, at a temperature between −100° C. and 0° C. then quenching of the reaction mixture with a mineral acid such as hydrochloric acid, yields the aryl ketone 2.

Scheme f.

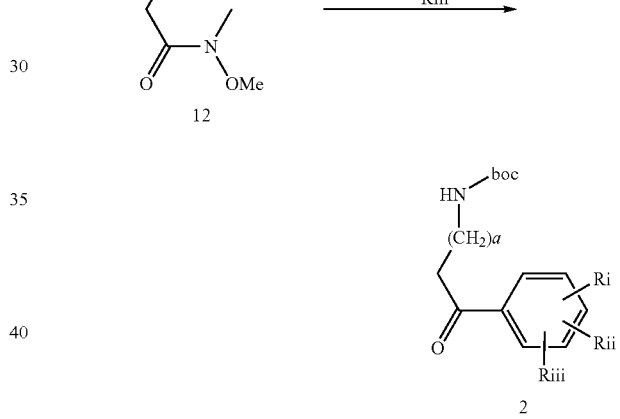

Commencing with a readily available amino acid with a suitable chain length [a] 11, the nitrogen atom can be brought in at the beginning of the synthesis by the route shown in Scheme f. Protection of the amine group of 11 with a tert-butylcarbamate group is achieved by condensation with di-tert-butyl di-carbonate in the presence of an amine base, for example triethylamine, in an inert solvent such as methylene chloride, chloroform, benzene, toluene, tetrahydrofuran and mixtures thereof and the like, at a temperature of −10° C. to 25° C. Coupling of the acid product with N,N-dimethylhydroxylamine in the presence of a coupling reagent 1-(3-dimethylaminopropyl)-3-ethylcarbodiimide hydrochloride (EDC) or 1,3-dicyclohexylcarbodiimide (DCC) or the like, with or without 1-hydroxybenotriazole (HOBt), and suitable amine base, such as triethylamine and the like, in an inert solvent such as methylene chloride, chloroform, dimethylformamide, or mixture thereof, at or near room temperature for a period of 3 to 24 hours provided the corresponding coupled product 12. Following the same route described above for scheme d, the aryl group can then be installed.

Scheme g.

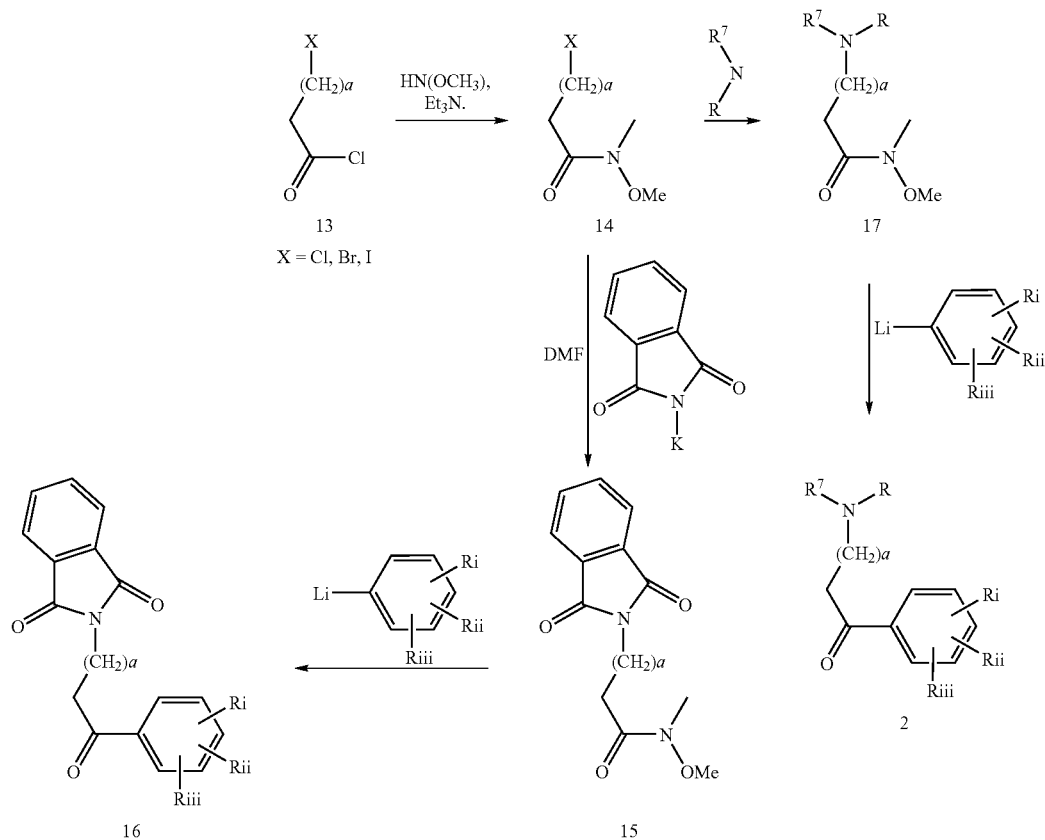

Scheme g illustrates another method for the synthesis of ketone such as 2 and 16, where the nitrogen group is introduced at a latter stage. As above a Weinreb amide 14 can be synthesised from an acid chloride. Treatment with the required amine, in an inert solvent such as THP, toluene, water and the such like can displace the group X to give 17. As above the aryl group can be introduced by displacement of the Weinreb amide with a suitable aryl lithium nucleophile. Alternatively the nitrogen atom can be introduced already protected as a phthalimide by displacement of the group x by potassium phthalimide, or similar salt thereof, by heating in an inert polar solvent such as DNF, DMSO, THF, toluene with or without the presence of a catalyst such as tetrabutylammonium iodide and the such like, to yield the compound 15. Again displacement of the Weinreb amide with an organolithium species completes the synthesis of a ketone suitable for cyclization under the Fischer condition described above for thienopyrrole synthesis.

Scheme h.

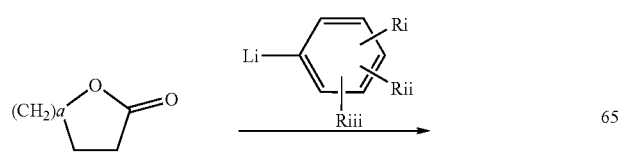

-continued

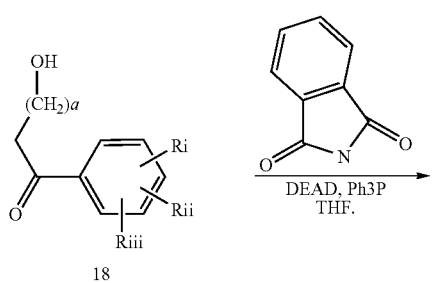

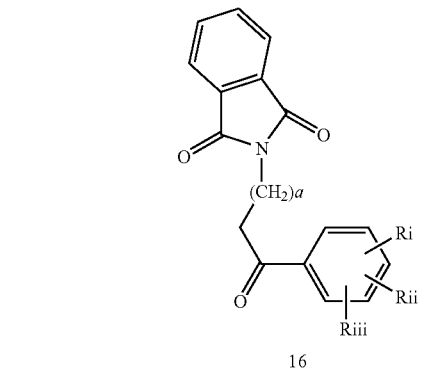

An alternative approach to a phthalimide protected nitrogen ketone, such as 16, can be taken by firstly treating a lactone, with an organolithium species as in the above schemes in a suitable solvent such as THF or ether at a low temperature of between −100° C. and −50° C. to yield a primary alcohol 18 (Scheme h). The hydroxyl function of 18 is replaced with a phthalimide group by a Mitsunobu reaction with an activating agent such as diethyldiazocarboxylate (DEAD), diisopropyldiazocarboxylate or the like with triphenylphosphine, tri-butylphosphine and the like, in an inert solvent such as benzene, toluene, tetrahydrofuran or mixtures thereof to give the desired ketone 16.

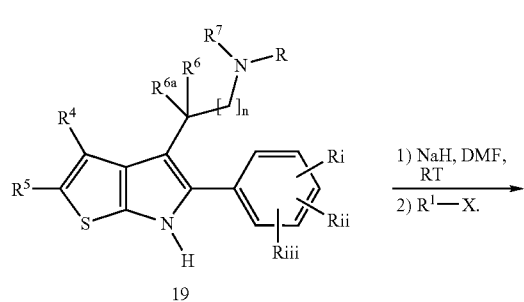

If the group $R^1$ was not present on the starting hydrazine before cyclization to form an thienopyrrole it may be added post cyclization by an alkylation reaction (19→3). The thienopyrrole is de-protonated by a strong base, such as sodium hydride, n-butyl lithium, lithium diisopropylamine, sodium hydroxide, potassium tert-butoxide in a suitable inert solvent such as THF, DMF, DMSO and the such like, and an alkyl halide added and the mixture stirred at room temperature.

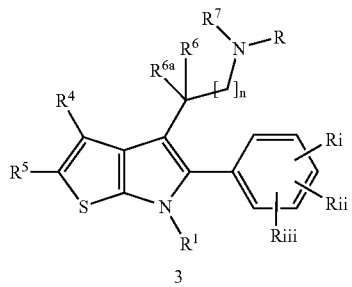

Scheme i

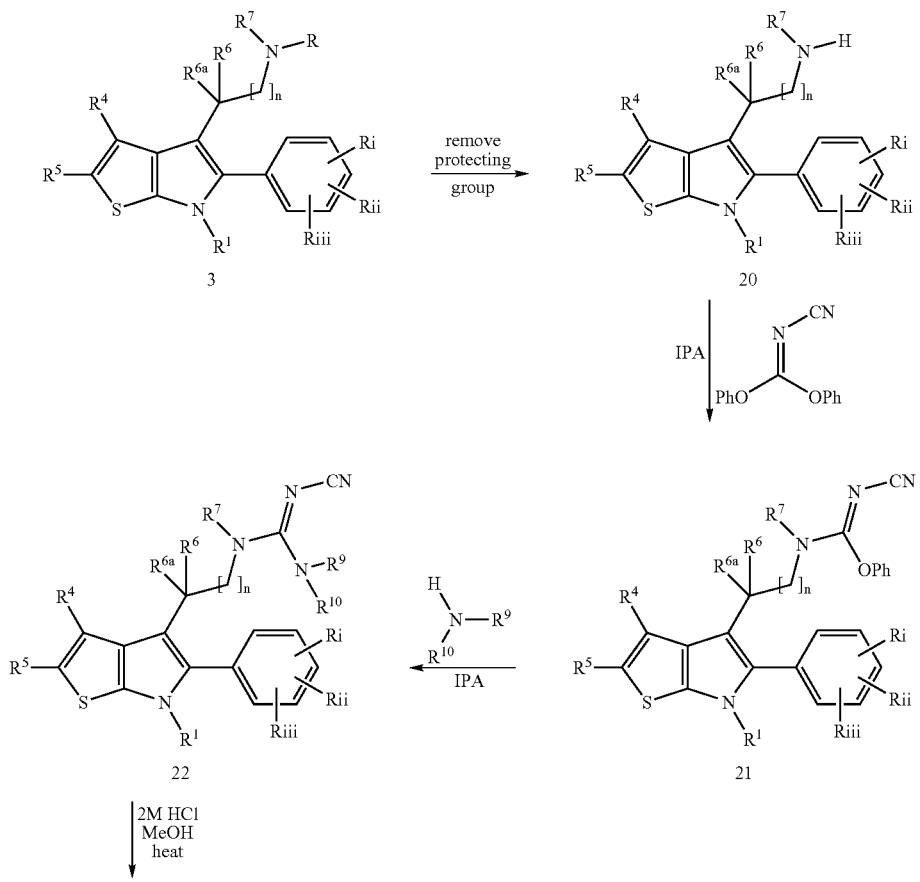

-continued

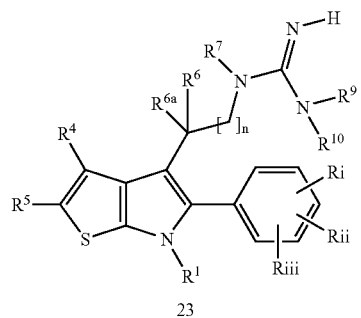
23

Depending on the route used above a thienopyrrole 20 suitable for conversion to a cyano-guandine can be formed by removal of the protecting group, for example if a tert-butylcarbamate group was used then removal is accomplished using a strong acid, for example trifluoroacetic acid or hydrochloric acid in an inert solvent such as methylene chloride, chloroform, THF or dioxane at a temperature between −20° C. and 25° C. A phthalimide group, for example, can be removed by hydrazine in a suitable solvent for example methanol, ethanol, methylene chloride, chloroform, THF dioxane at a temperature between −20° C. and 25° C. The primary amine 20 can be converted to a cyano-guanidine 22 by the two step process of reaction with diphenyl cyanocarbonimidate in an inert organic solvent such as iso-propyl alcohol, methylene chloride, chloroform, benzene, tetrahydrofuran and the like, at a temperature between −20° C. and 50° C., followed by condensation with an appropriately substituted amine in an inert organic from the list above, with heating at a temperature between −20° C. and 100° C. (Scheme I 20→21→22). Further treatment of 22 with 2 molar Hydrochloric acid in methanol at elevated temperature yields guanidine compounds 23.

Scheme j.

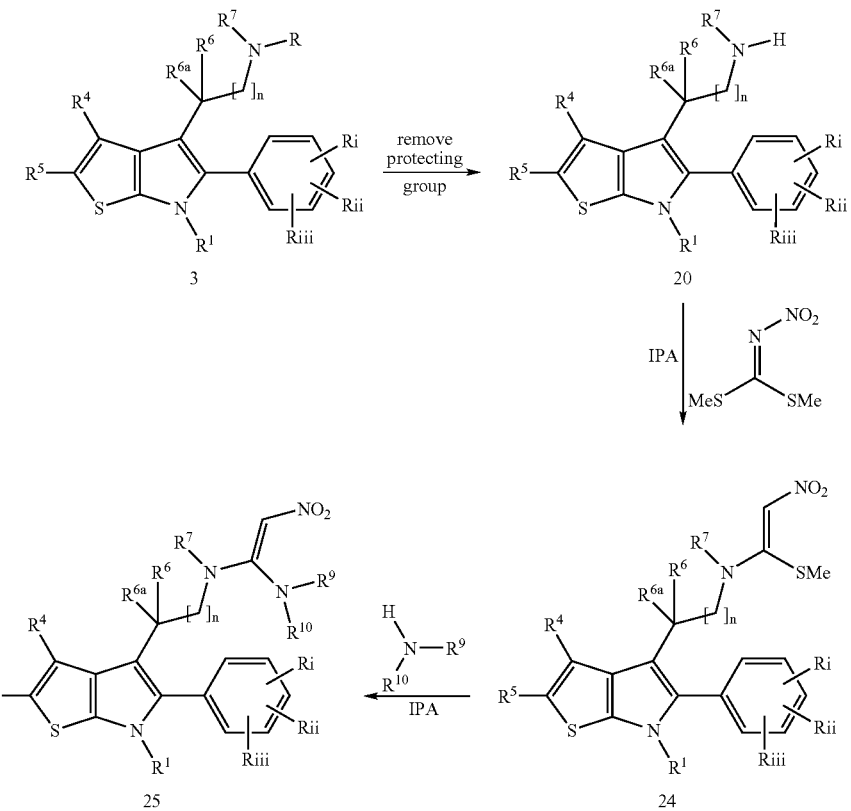

Similarly, reaction with 1,1'-bis(methylthio)-2-nitroethylene in an inert solvent such methylene chloride, chloroform, benzene, tetrahydrofuran and the like, followed by condensation with an appropriately substituted amine in an inert organic solvent from the list above yields the nitroethyleneimidazo[1,2-α]pyridine 25 (Scheme j, 20→24→25).

Scheme k.

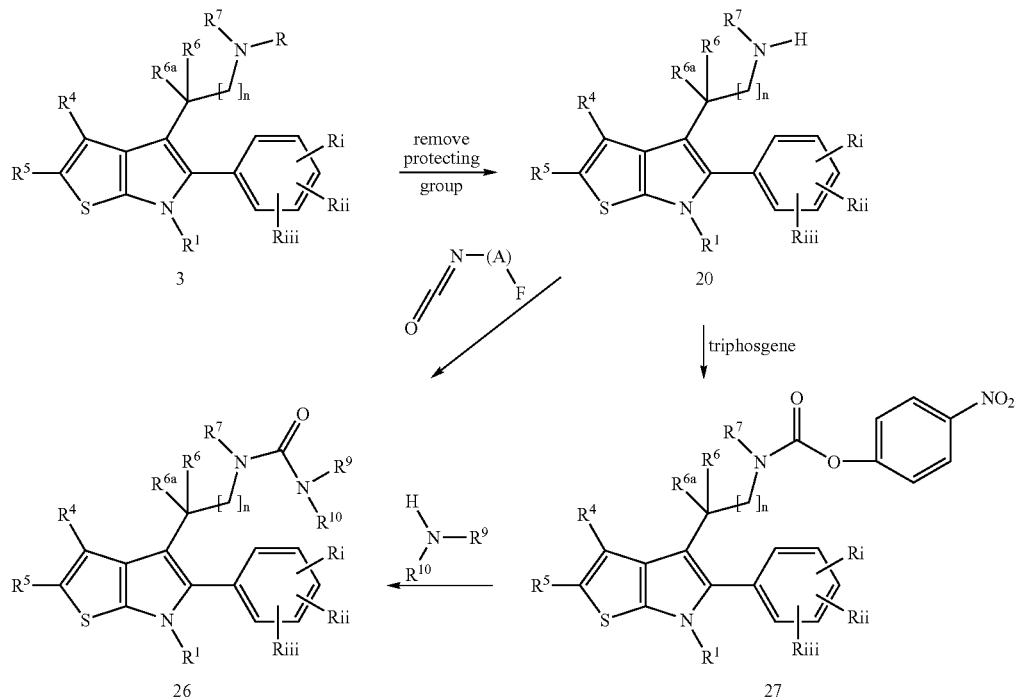

Again in a similar fashion the suitable thienopyrrole 20, derived from de-protection, can be converted to a urea by either direct treatment with an iso-cyanate in an inert solvent such as methylene chloride, chloroform or ThF and the such like, or by a two step procedure of reaction with triphosgene (20→27) followed by addition of an amine (27→26), bearing the required substitution to yield 26.

EXAMPLES

The invention will now be illustrated with the following non-limiting Examples in which, unless otherwise stated:

(i) evaporations were carried out by rotary evaporation *in vacuo* and work-up procedures were carried out after removal of residual solids such as drying agents by filtration;

(ii) operations were carried out at room temperature, that is in the range 18-25° C. and under an atmosphere of an inert gas such as argon or nitrogen;

(iii) yields are given for illustration only and are not necessarily the maximum attainable;

(iv) the structures of the end-products of the Formula (I) were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; mn, multiplet; br, broad; q, quartet, quin, quintet;

(v) intermediates were not generally fully characterised and purity was assessed by thin layer chromatography (TLC), high-performance liquid chromatography (HPLC), infra-red (IR) or NMR analysis;

(vi) chromatography was performed on silica (Merck Keiselgel: Art.9385);

(vii) isolute™ refers to silica ($SiO_2$) based columns with irregular particles with an average size of 50 μm with nominal 60 Å porosity [Source: Jones Chromatography, Ltd., Glamorgan, Wales, United Kingdom].

| Abbreviations | |
|---|---|
| brine | a saturated solution of sodium chloride in distilled water |
| DCC | 1,3-dicyclohexylcarbodiimide |
| DEAD | diethyldiazocarboxylate |
| DMSO | Dimethyl sulphoxide |
| DMF | dimethylformamide |
| EDC | 1-(3-dimethylaminopropyl)-3-ethylcarbodiimide hydrochloride |
| HOBt | 1-hydroxybenotriazole |
| IPA | isopropyl alcohol |
| RM | reaction mixture |
| RT | room temperature |
| THF | tetrahydrofuran |

Starting Materials

The starting materials were prepared as follows:

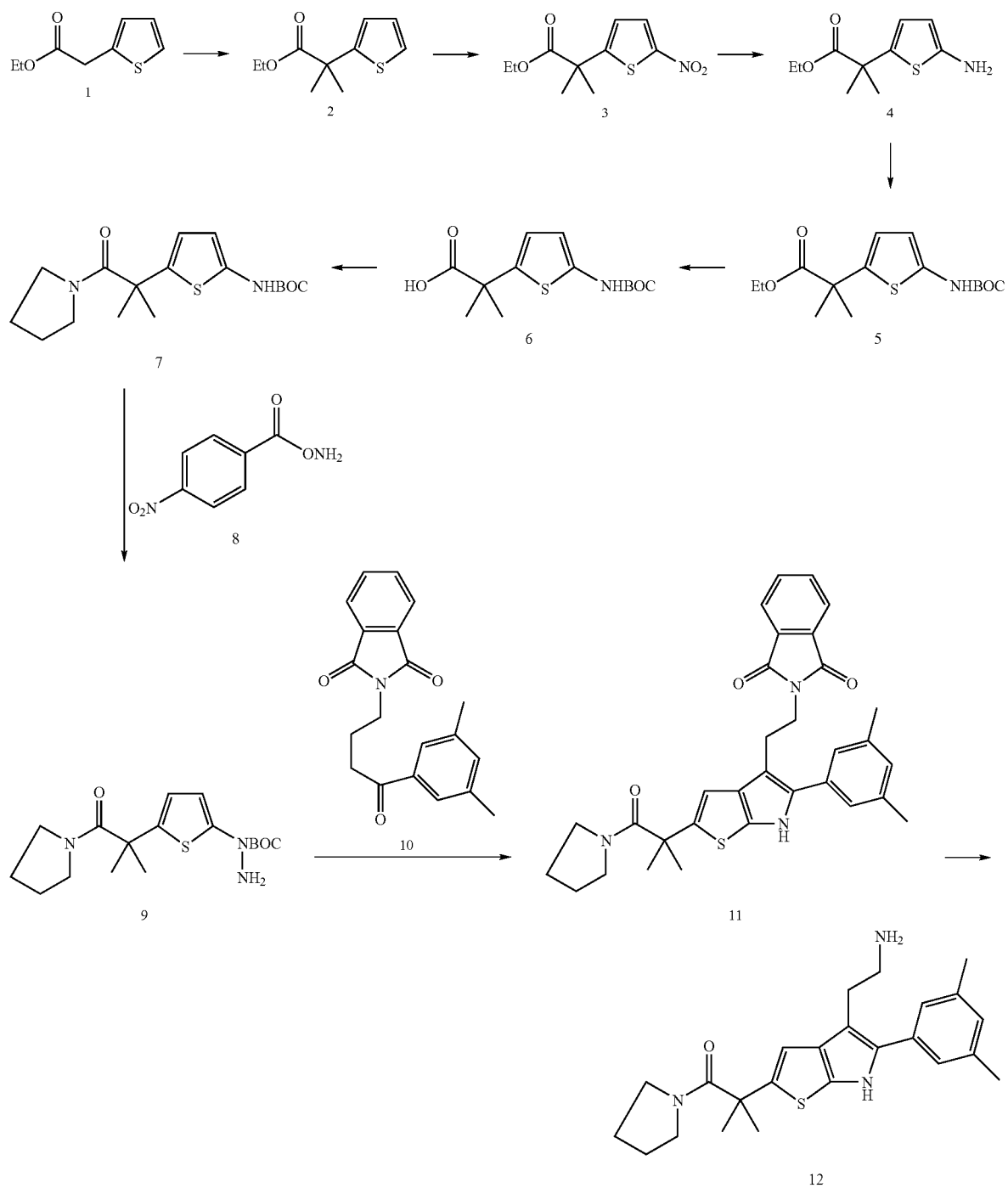

To a suspension of NaH (54 g; 1.35 mol), and 18-crown-6 in THF (2 l) stirred at ambient temperature under argon atmosphere, 1 (100 g; 0.588 mol) was added over a period of 30 minutes. After stirring overnight, the mixture was cooled at 0° C. and methyl iodide was added dropwise. The mixture was stirred at 18° C. for 3 hours, poured into a saturated solution of NH$_4$Cl and extracted with AcOEt. The organic phase was evaporated and purified by flash chromatography eluting with petroleum ether/ethyl acetate 95/5 to give 2 as an oil.

Yield: 90% $^1$H NMR (CDCl$_3$): 1.20 (t, 3H); 1.63 (s, 6H); 4.10 (q, 2H); 6.92 (m, 2H); 7.17 (m, 1H).

Nitronium tetrafluoroborate (77.9 g; 0.586 mol) was added at −55° C. to a solution of 2 (105.6 g; 0.583 mol) in DME (1.5 l). The mixture was allowed to warm up at −10° C. over 4 hours. After extraction with ethyl acetate, the organic phase was purified by flash chromatography, eluting with petroleum ether/AcOEt 95/5 to give 3.

Yield: 86% $^1$H NMR (CDCl$_3$): 1.23 (t, 3H); 1.65 (s, 6H); 4.14 (q, 2H); 6.90 (d, 1H); 7.75 (d, 1H).

A suspension of 3 (101.7 g; 0.41 mol) and 10% Pd/C (15 g) in a mixture of ethanol (700 ml) and ethyl acetate (300 ml) was hydrogenated under hydrogen atmosphere (5 bars) for 5 hours. After filtration of the catalyst on celite, the residue was evaporated and redissolved in THF (900 ml); di-tert-butyl dicarbonate (100 g; 0.46 mol) was added and the mixture was refluxed for 16 hours. After evaporation of the solvents, the resulting solid was taken up in petroleum ether and filtered to give 5.

Yield: 68% $^1$H NMR (CDCl$_3$): 1.20 (t, 3H); 1.48 (s, 9H); 1.58 (s, 6H); 4.10 (q, 2H); 6.30 (m, 1H); 6.60 (m, 1H).

A solution of 5 (50 g; 0.16 mol) and 2N NaOH (160 ml) in ethanol (300 ml) was refluxed for 1 h 30. After evaporation to dryness, the residue was partitioned between water and ether. The aqueous layer was acidified with saturated citric acid and extraction with ethyl acetate to give after evaporation a solid, which was triturated in pentane and filtered to give 6 as a solid.

Yield: 100% $^1$H NMR (DMSOd$_6$): 1.48 (m, 15H); 6.30 (d, 1H); 6.59 (d, 1H).

A solution of 6 (20.1 g; 0.07 mol), EDCI (20.1 g; 0.105 mol) and DMAP (2.56 g; 0.021 mol) in dichloromethane (200 ml) was stirred under argon atmosphere for 10 minutes. Pyrrolidine (11.69 ml; 0.14 mol) was then added and the mixture was stirred overnight at ambient temperature. After evaporation to dryness, the residue was purified by flash chromatography eluting with AcOEt/petroleum ether 40/60 to give after trituration in ether/pentane 7 as a solid.

$^1$H NMR (CDCl$_3$): 1.51 and 1.57 (s, 15 H); 1.7 (m, 4H); 3.03 (br, 2H); 3.50 (br, 2H); 6.35 (d, 1H); 6.48 (d, 1H); 7.26 (br, 1H).

7 (17 g; 0.05 mol) was added under argon atmosphere to a suspension of NaH 60% (2.42 g; 0.06 mol) in dioxan (240 ml). The mixture was stirred at 100° C. for 3 hours. After cooling to 10° C., 8 (10.1 g; 0.055 mol) was added. The reaction mixture was stirred at ambient temperature overnight. After filtration of the insoluble, the filtrate was evaporated and purified by flash chromatography, eluting with AcOEt/petroleum ether 45/55 to give 9 as a white solid.

Yield: 89.5% $^1$H NMR (CDCl$_3$): 1.55 and 1.57 (s, 15 H); 1.71 (s, 4H); 3.04 (s, 2H); 3.50 (s, 2H); 6.53 (d, 2H); 6.70 (s, 2H).

A solution of 9 hydrochloride salt (4 g; 0.0102 mol) and 10 (6.6 g; 0.0205 mol) in AcOH (20 ml) was heated at 120° C. under argon atmosphere for 3 hours. The reaction mixture was diluted with saturated NH$_4$Cl and extracted with AcOEt. After evaporation, the crude was purified by flash chromatography eluting with AcOEt/petroleum ether 50/50 to give 11 as a foam.

Yield: 53% MS-ESI: 540 [M+H]$^+$ $^1$H NMR (CDCl$_3$): 1.53 and 1.58 (s, 6H); 1.69 (s, 4H); 2.29 (s, 6H); 3.12 (m, 4H); 3.52 (s, 2H); 3.91 (m, 2H); 6.80 (m, 2H); 7.02 (s, 2H); 7.6-7.8 (m, 4H); 8.10 (s, 1H).

A solution of 11 (0.534 g; 0.99 mmol) and hydrazine (1 ml) in a mixture of EtOH (2 ml) and CH$_2$Cl$_2$ (2 ml) was stirred under argon atmosphere at ambient temperature overnight. After evaporation, the crude was extracted in a mixture of CH$_2$Cl$_2$ and saturated NaHCO$_3$. The organic layer was evaporated to give 12 as a foam.

Yield: 90% $^1$H NMR (CDCl$_3$): 1.52 and 1.62 (s, 6H); 1.69 (s, 4H); 2.33 (s, 6H); 2.80-3.2 (m, 6H); 3.52 (m, 2H); 6.74 (s, 1H); 6.93 (s, 1H); 7.05 (s, 2H); 8.15 (s, 1H).

MS-ESI: 410 [M+H]$^+$

Example 1.0

N'-cyano-N-{2-[2-(1,1-dimethyl-2-oxo-2-pyrrolidin-1-ylethyl)-5-(3,5-dimethylphenyl)-6H-thieno[2,3-b]pyrrol-4-yl]ethyl}-3-pyridin-4-ylpyrrolidine-1-carboximidamide Example 1.1

N-{2-[2-(1,1-dimethyl-2-oxo-2-pyrrolidin-1-ylethyl)-5-(3,5-dimethylphenyl)-6H-thieno[2,3-b]pyrrol-4-yl]ethyl}-3-pyridin-4-ylpyrrolidine-1-carboximidamide

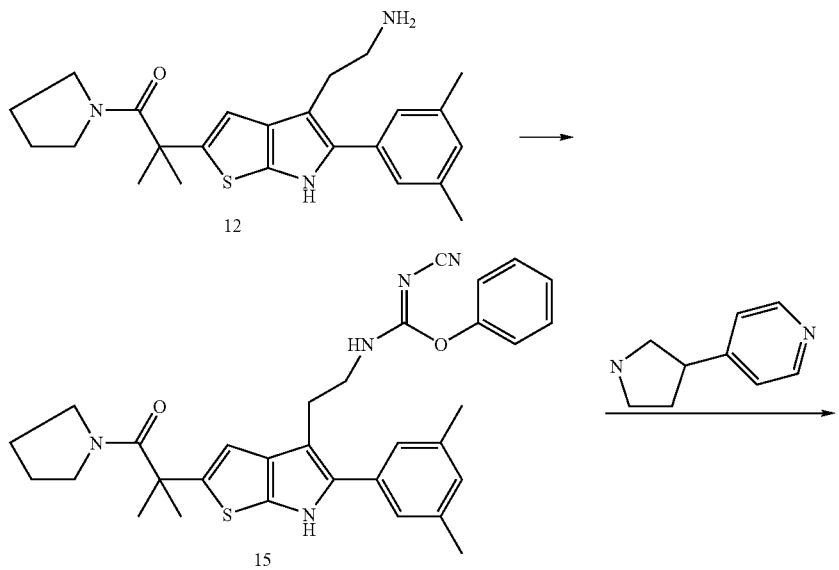

-continued

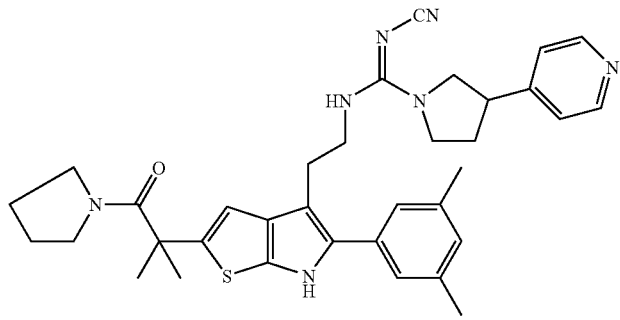

16
Example 1.0

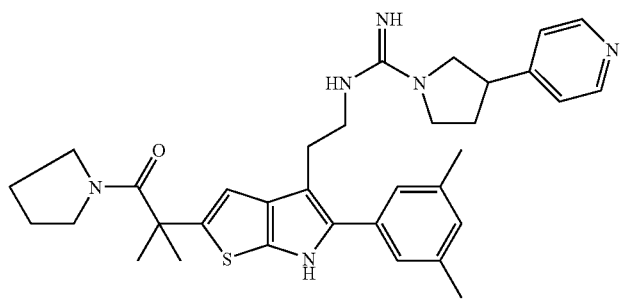

Example 1.1

A solution of 16 (0.160 g; 0.26 mmol) in a mixture of MeOH (8 ml) and 2N HCl (8 ml) was heated at 70° C. for 18 hours.

After neutralisation with diluted NH$_4$OH, the mixture was extracted with AcOEt/PrOH 10/3. The organic layer was evaporated and purified by flash chromatography eluting with a gradient 5-20% 3.5N—NH$_3$-MeOH/CH$_2$Cl$_2$ to give Example 1.1.

Yield: 20% MS-ESI: 583 [M+H]$^+$ $^1$H NMR (DMSO d6): 1.53 (s, 6H); 1.64 (m br, 4H); 2-2.15 (m, 1H); 2.3 (s, 6H); 2.4-2.5 (m br, 1H); 3-3.10 (m, 4H); 3.35-3.5 (m, 7H); 3.8 (m br, 2H); 6.83 (s, 1H); 6.91 (s, 1H); 7.09 (s, 2H).

The starting material was prepared as follows:

A solution of 12 (0.527 g; 1.288 mmol) and diphenyl-N-cyanocarbonimidate (0.522 g; 2.19 mmol) in isopropanol (10 ml) was stirred at ambient temperature under argon atmosphere for 20 hours. After evaporation to dryness, the crude was purified by flash chromatography, eluting with petroleum ether/AcOEt 80/20 to give 15.

Yield: 56%. MS-ESI: 554 [M+H]$^+$

A mixture of 15 (0.38 g; 0.68 mmol) and 4-pyrrolidin-3-yl pyridine (0.38 g; 2.5 mmol) in isopropanol was refluxed under argon atmosphere for 20 hours. After evaporation to dryness, the mixture was purified by flash chromatography, eluting with a gradient 4-8% MeOH/CH$_2$Cl$_2$ to give Example 1.0.

Yield: 66%. MS-ESI: 606 [M−H]$^-$ $^1$H NMR (CDCl$_3$): 1.62 (s, 6H); 1.6-1.7 (m br, 4H); 1.85-2 (m, 1H); 2.2-2.35 (m, 1H); 2.3 (s, 6H); 3.05-3.8 (m, 13 H); 4.4 (t, 1H NH); 6.73 (s, 1H); 6.88 (s, 1H); 7.04 (d, 2H); 7.05 (s, 2H); 8.47 (s, 1H 1NH); 8.52 (d, 2H).

Examples 1.2-1.6

Following a procedure similar to that described in example 1, the following compounds were prepared.

| Example | | MS-ESI |
|---|---|---|
| 1.2 | 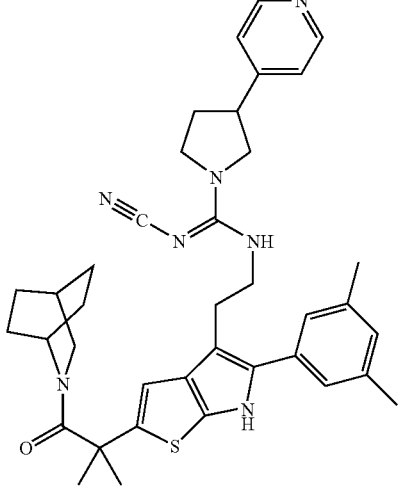 | 648 [M + H]+ |
| 1.3 | 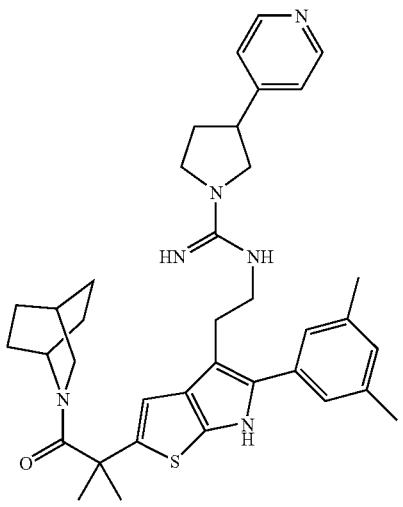 | 623 [M + H]+ |
| 1.4 | 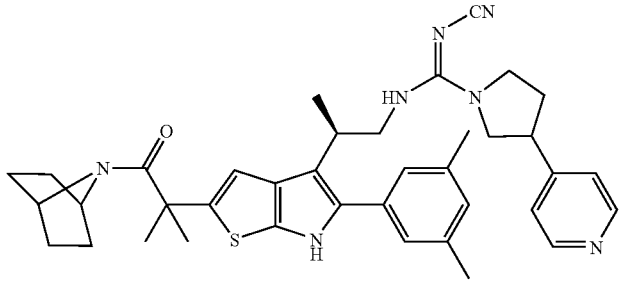 | 648 [M + H]+ |
| 1.5 | 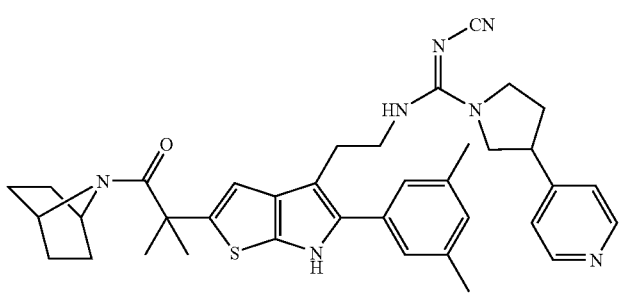 | 634 [M + H]+ |

-continued
| Example | | MS-ESI |
|---|---|---|
| 1.6 | 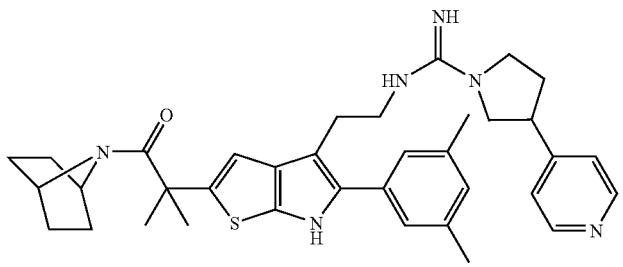 | 609 [M + H]⁺ |
Example 2
2-(1,1-dimethyl-2-oxo-2-azabicyclo[2.2.1]heptan-7-ylethyl)-4-[1S-methyl-2-(N'-isopropoxycarbonyl-3-pyrid-4-yl-pyrrolidin-1-ylcarboximidamido)ethyl]-5-(3,5-dimethylphenyl)-6H-thieno[2,3-b]pyrrole
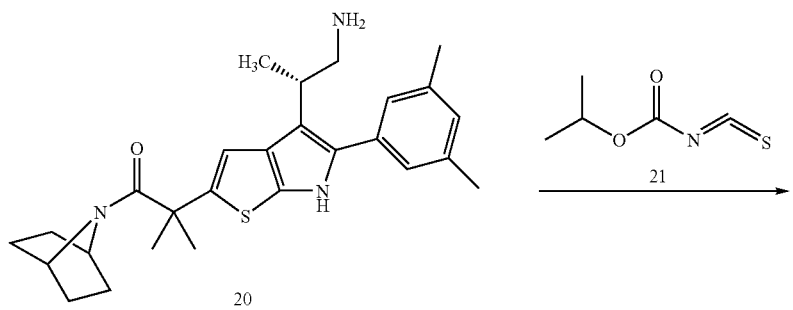
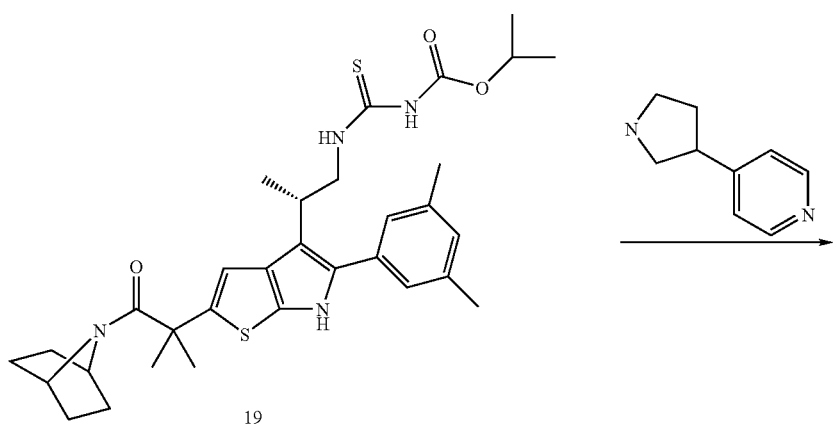

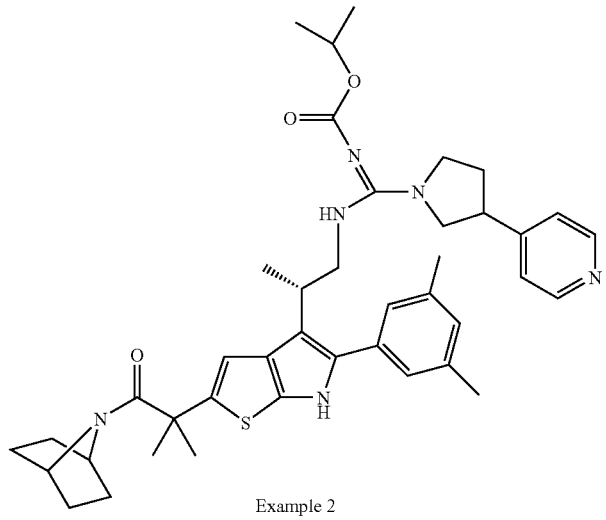

Example 2

To a solution of 19 (0.325 g; 0.54 mmol) in CH$_2$Cl$_2$ (10 ml) at 0° C. was added under argon atmosphere 4-pyrrodidin-3-yl pyridine (0.122 g; 0.82 mmol), EDC (0.158 g; 0.82 mmol) and DIEA (0.142 ml; 0.82 mmol). The mixture was stirred at 0° C. for 15 minutes allowed to warm up and stirred for 24 hours at ambient temperature. The reaction mixture was extracted with CH$_2$Cl$_2$. The organic layer was evaporated and the crude material was purified by flash chromatography eluting with AcOEt and MeOH—NH$_3$ 97.5/2.5 95/5 to give Example 2 as a solid.

Yield: 55%. $^1$H NMR (CDCl$_3$): 1.2 (m, 6H); 1.2-1.3 (m, 4H); 1.4 (m, 3H); 1.5-1.68 (m, 4H); 1.55 (s, 6H); 1.7-1.9 (m, 1H); 2.1-2.2 (m, 1H); 2.28 (m, 6H); 3.02-3.5 (m, 7H); 3.6 (m, 1H); 4.05 (s broad, 1H); 4.7 (s broad, 1H); 4.82 (m, 1H); 6.72 (s, 1H); 6.9 (m, 1H); 7.0 (s, 1H); 7.05 (d, 2H); 8.20 (s, 1H); 8.50 (d, 2H) MS-ESI: [M+H]$^+$ 709

The starting material was prepared as follows:

To a solution of 21 (0.098 g; 0.66 mmol) in CH$_2$Cl$_2$ (1.5 ml) was added at 0° C., a solution of 20 (0.3 g; 0.66 mmol) in CH$_2$Cl$_2$ (1.5 ml). The mixture was stirred at ambient temperature for 90 minutes and extracted. The organic layer was evaporated and purified by flash chromatography, eluting with CH$_2$Cl$_2$/AcOEt 50/50 to give 19.

Yield: 90% $^1$H NMR (CDCl$_3$): 1.2 (m, 6H); 1.2-1.35 (m, 4H); 1.38 (d, 3H); 1.50-1.80 (m, 4H); 1.55 (s, 6H); 2.35 (s, 6H); 3.45 (m, 1H); 1.78 (m, 1H); 4.00 (m, 1H); 4.10 (s broad 1H); 4.75 (s broad, 1H); 4.87 (m, 1H); 6.80 (s, 1H); 6.96 (s, 1H); 7.07 (s, 2H); 7.72 (s, 1H); 8.10 (s, 1H); 9.54 (s, 1H). MS-ESI: [M+H]$^+$ 595

Preparation of 20 is described in Example 8.

Examples 2.1-2.7

Following a procedure similar to that described in example 3, the following examples were prepared.

| Example | | MS-ESI |
|---|---|---|
| 2.1 | | 695 [M + H]$^+$ |

-continued
| Example | | MS-ESI |
|---|---|---|
| 2.2 | 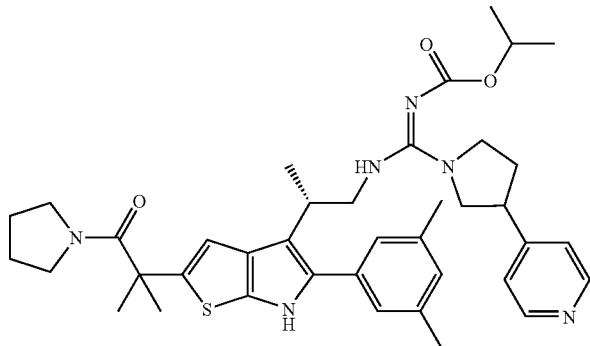 | 683 [M + H]+ |
| 2.3 | 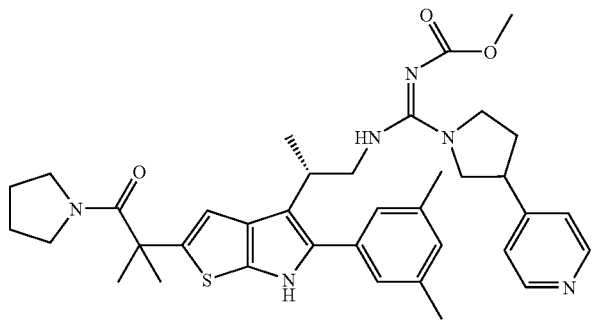 | 655 [M + H]+ |
| 2.4 | 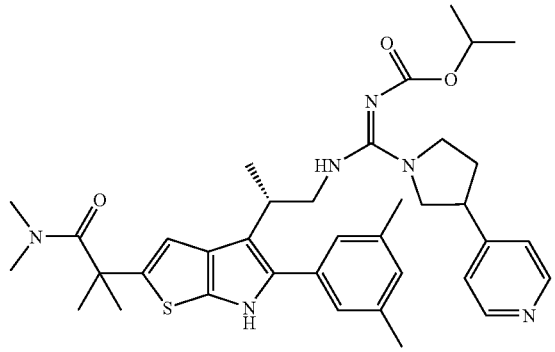 | 657 [M + H]+ |
| 2.5 | 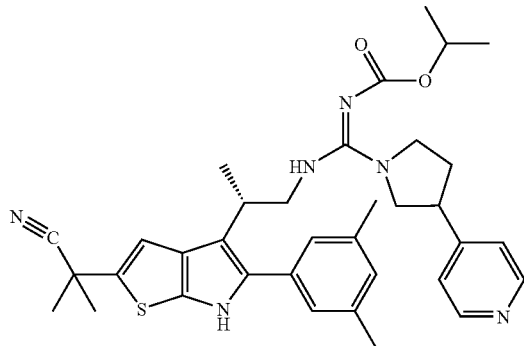 | 611 [M + H]+ |

-continued
| Example | | MS-ESI |
|---|---|---|
| 2.6 | 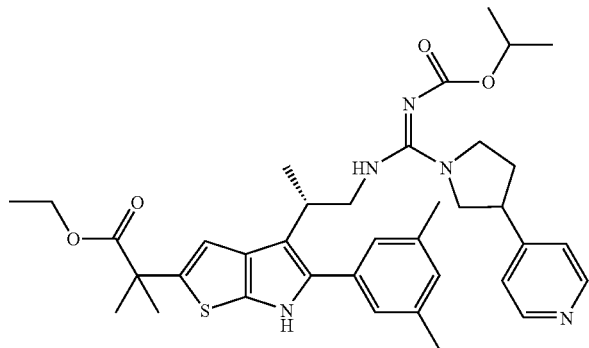 | 658 [M + H]+ |
| 2.7 | 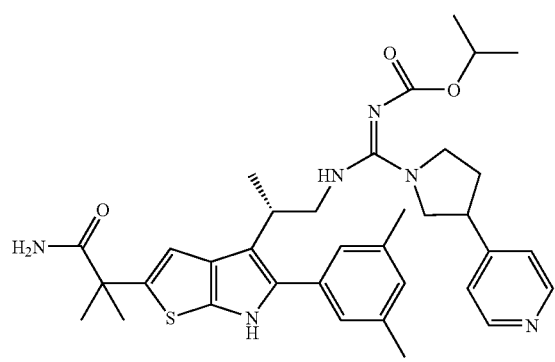 | 629 [M + H]+ |
| 2.8 | 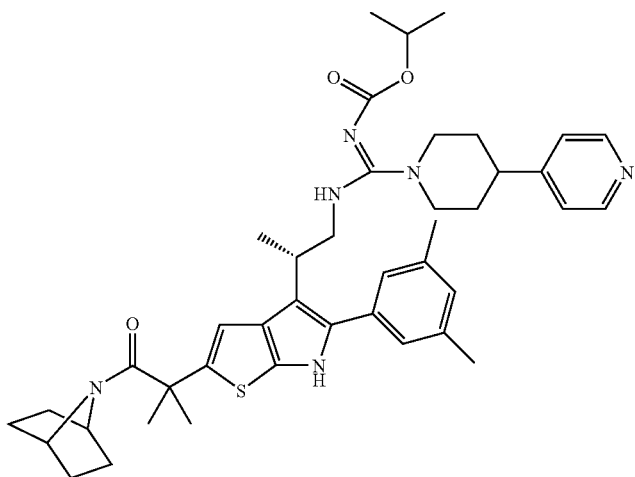 | 724 [M + H]+ |

-continued
| Example | | MS-ESI |
|---|---|---|
| 2.9 | 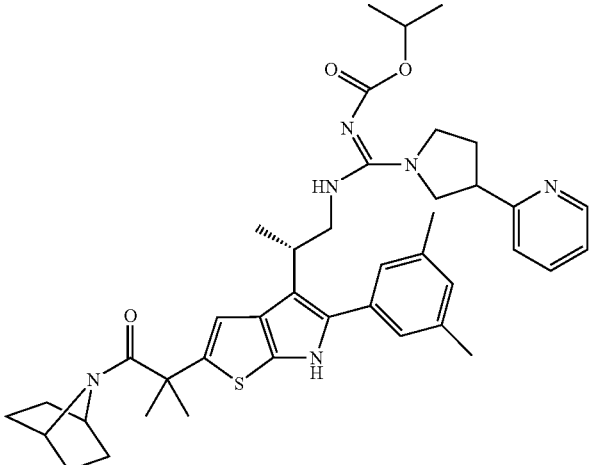 | 709 [M + H]+ |
| 2.10 | 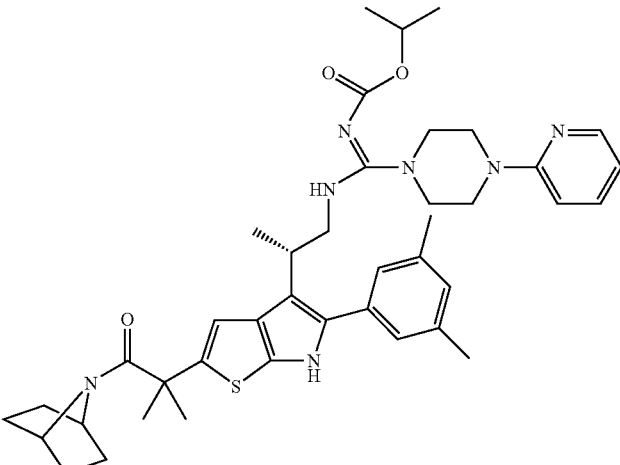 | 724 [M + H]+ |
| 2.11 | 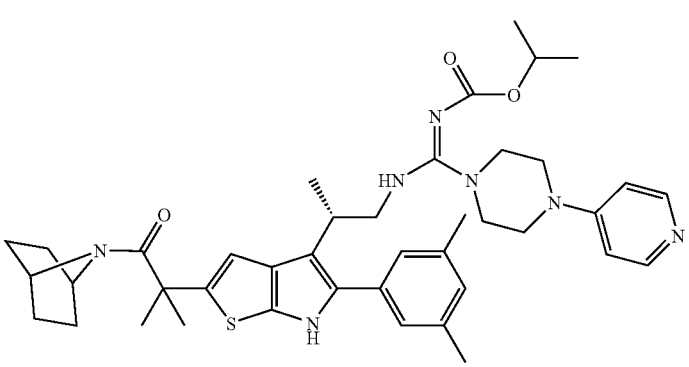 | 724 M + H]+ |

| Example | | MS-ESI |
|---|---|---|
| 2.12 | 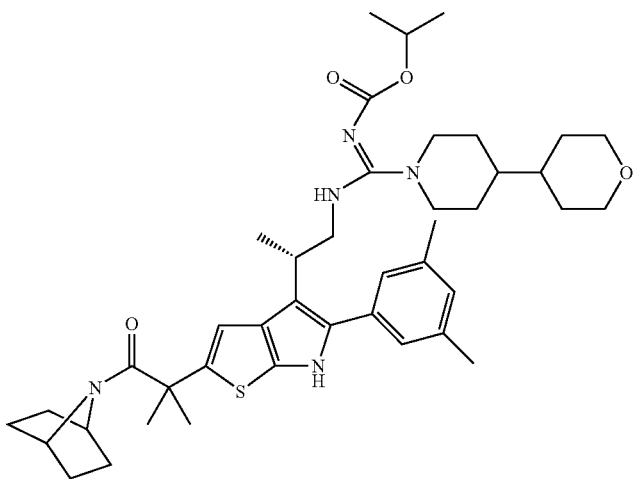 | 730 M + H]+ |
| 2.13 | 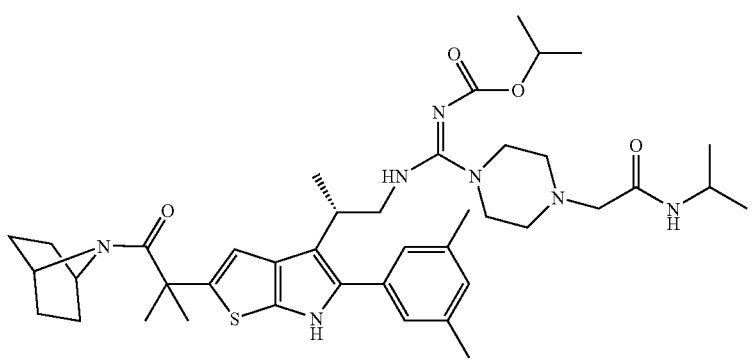 | 746 M + H]+ |
Example 3
2-(1,1-dimethyl-2-oxo-2-pyrrolidin-1-ylethyl)-4-[1S-methyl-2-(3-{pyridin-4-yl}pyrrolidin-1-yl)carbony-lamino-ethyl]-5-(3,5-dimethylphenyl)-6H-thieno[2,3-b]pyrrole
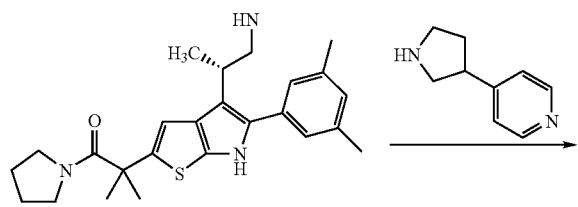
-continued
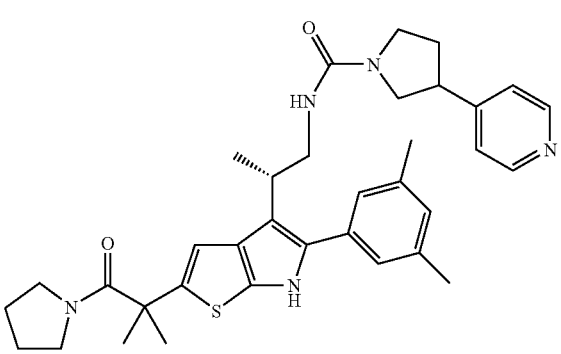
Example 3

4-nitrophenyl chloroformate (0.127 g; 0.63 mmol) was added under argon atmosphere, at 0° C. to a solution of 22 (0.254 g; 0.60 mmol) and triethylamine −0.088 ml; 0.63 mmol) in methylene chloride (4 ml). The mixture was stirred at 0° C. for 30 minutes and at ambient temperature for 1 hour. 4-pyrrolidin-3-yl pyridine (0.098 g; 0.72 mmol) in solution in methylene chloride (0.5 ml) was added. The mixture was stifled for 2 hours and purified by flash chromatography eluting with a gradient 2-6% MeOH/CH$_2$Cl$_2$ to give Example 3 as a solid.

Yield: 80% MS-ESI: 598 [M+M]$^+$ $^1$HNMR (CDCl$_3$): 1.37 (d, 3H); 1.6 (s, 6H); 1.6-1.75 (m, 4H); 1.75-2 (m, 1H); 2.2-2.3 'm, 1H); 2.29 (s, 6H); 3-3.4 (m, 8H); 3.45-3.8 (m, 4H); 4.12 (m, 1H, NH); 6.77 (s, 1H); 6.91 (m, 1H); 7-7.1 (m, 4H); 8.28 (s, 1H, NH); 8.48 (s, br, 2H).

22 was prepared following a procedure similar to that described in example 1 for compound 12.

Examples 3.1-3.5

Following a procedure similar to that described in example 4, the following examples were prepared.

| Example | | MS-ESI |
|---|---|---|
| 3.1 | 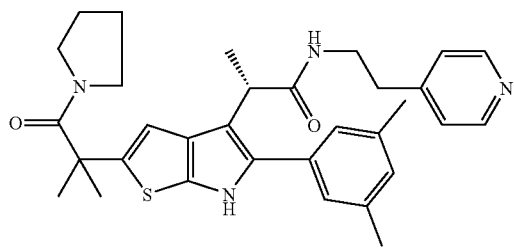 | 572 [M + H]$^+$ |
| 3.2 | 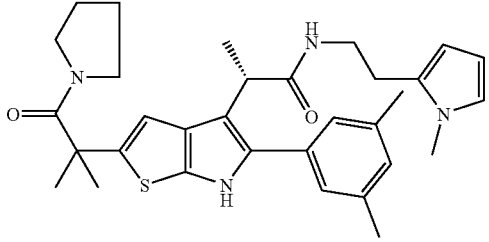 | 574 [M + H]$^+$ |
| 3.3 | 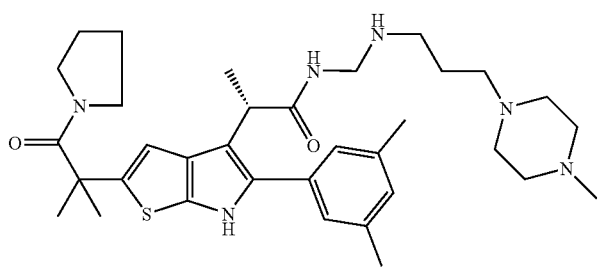 | 607 [M + H]$^+$ |
| 3.4 | 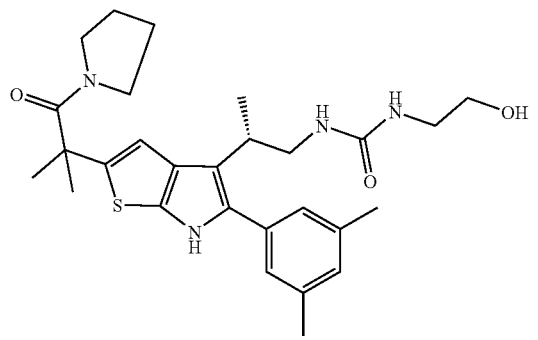 | 520 [M + H]$^+$ |

| Example | | MS-ESI |
|---|---|---|
| 3.5 | 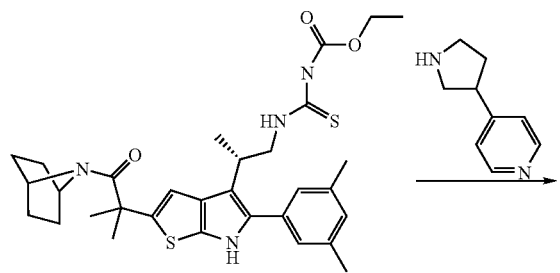 | 624 [M + H]+ |
| 3.6 | | 638 [M + H]+ |

Example 4

2-(1,1-dimethyl-2-oxo-2-azabicyclo[2.2.1]heptan-7-ylethyl)-4-[1S-methyl-2-(N'-ethoxycarbonyl-3-pyrid-4-yl-pyrrolidin-1-ylcarboximidamido)ethyl]-5-(3,5-dimethylphenyl)-6H-thieno[2,3-b]pyrrole Example 4 was prepared following a procedure similar to that described in example 2.

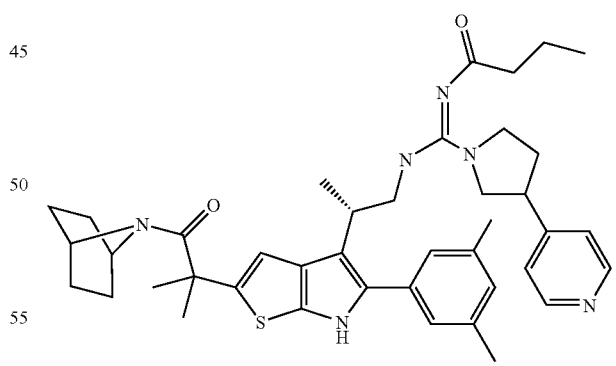

Example 4

Yield: 63% $^1$H NMR (CDCl$_3$) 1.25 (multiplet, 3H); 1.25-1.38 (m, 6H); 1.43 (multiplet, 3H); 1.62 (s, 6H); 1.45-2.20 (multiplets, 5H); 2.32 (s, 6H); 3.00-3.55 (multiplets, 7H); 3.65 (multiplet, 1H); 4.1 (sb, 1H); 4.07 (multiplet, 2H); 4.80 (sb, 1H); 6.75 (s, 1H); 6.93 (d, 1H); 7.02 (m,3H); 7.07 (d, 1H); 8.27 (s, 1H); 8.51 (multiplet, 2H). MS-ESI: 695 [M+H]+

The starting material was prepared as follows:

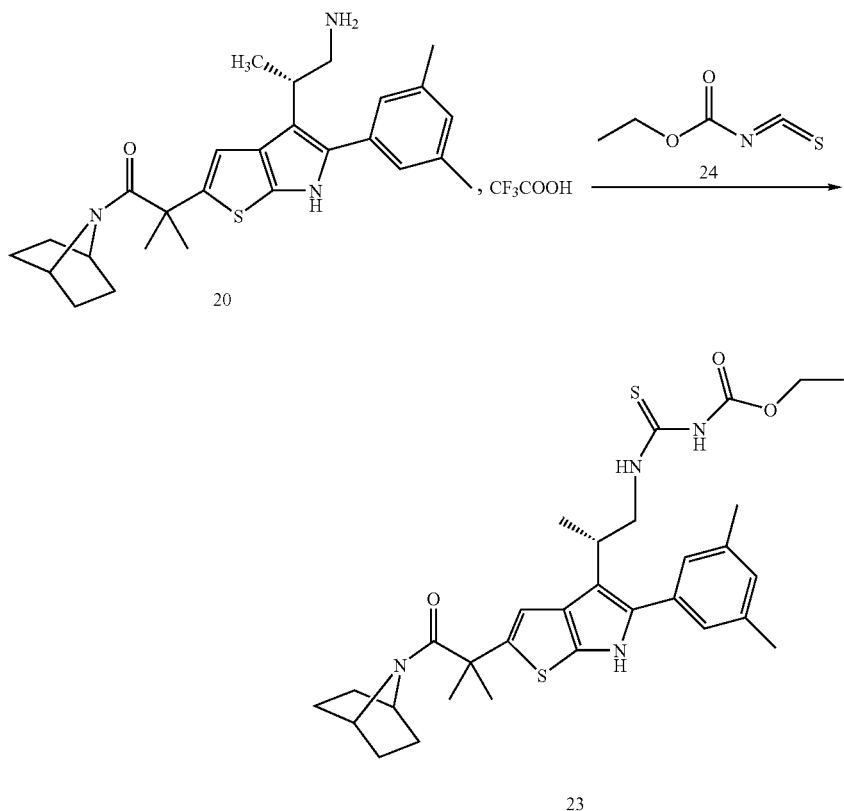

To a solution of 24 (0.350 g; 2.66 mmol) in CH$_2$Cl$_2$ (8 ml) was added at 0° C., a solution of 20 (1.5 g; 2.66 mmol) and DIEA (0.463 ml; 2.66 mmol) in CH$_2$Cl$_2$ (8 ml). The mixture was stirred at ambient temperature for 2 hours. After evaporation, the residue was purified by flash chromatography, eluting successively with CH$_2$Cl$_2$ and CH$_2$Cl$_2$/AcOEt 585/15 to give 23.

Yield: 100% $^1$H NMR (CDCl$_3$) 1.209 (t, 3H); 1.25-1.55 (m, 4H); 1.45-1.80 (m, 4H); 1.627 (d, 3H); 1.591 (s, 6H); 2.355 (s, 6H); 3.473 (multiplet, 1H); 3.770 (multiplet, 1H); 4.05 (quintuplet, 1H); 4.1 (sb, 1H); 4.130 (quadruplet, 2H); 4.85 (sb, 1H); 6.806 (s, 1H); 6.968 (s, 1H); 7.069 (s, 2H); 7.799 (s, 1H) 8.129 (s, 1H); 9.55 (s, 1H).

Example 5

2-(1,1-dimethyl-2-oxo-2-azabicyclo[2.2.1]heptan-7-ylethyl)-4-[1S-methyl-2-(N'-isoethoxycarbonyl-4-{morpholinocarbonyl}piperazin-1-yl carboximidamido)ethyl]-5-(3,5-dimethylphenyl)-6H-thieno[2,3-b]pyrrole

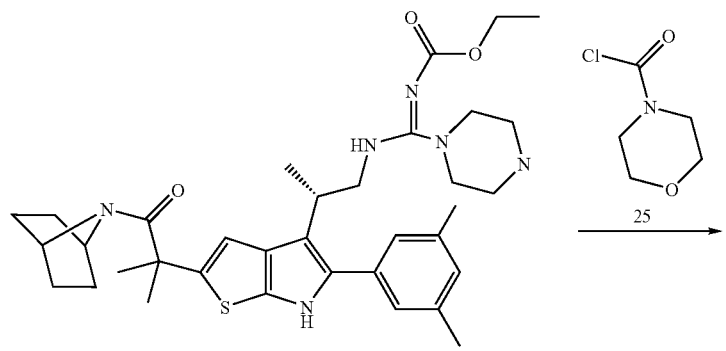

-continued

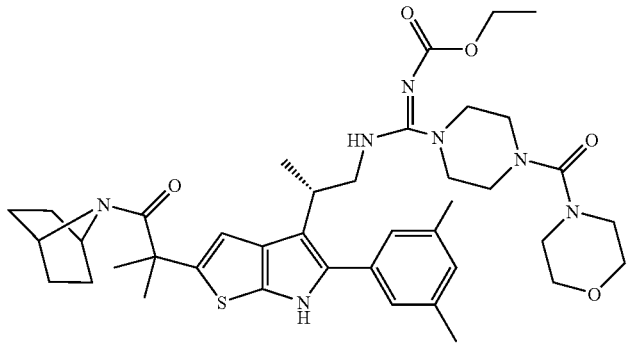

Example 5

To a mixture of 24 (0.095 g; 0.15 mmol) and K$_2$CO$_3$ (0.23 g: 0.165 mmol) in CH$_3$CN (3 ml) was added under argon atmosphere, 25 (0.025 g; 0.165 mmol). The mixture was stirred at ambient temperature for 20 hours. After evaporation to dryness, the residue was purified by flash chromatography, eluting successively with CH$_2$Cl$_2$, CH$_2$Cl$_2$/AcOEt 50/50 and NH3/AcOEt 2/98 to give after trituration in ether:pentane Example 5 as a solid.

Yield: 72%. $^1$H RMN (CDCl$_3$)1.270 (t, 3H); 1.20-1.35 (m, 4H); 1.392 (d, 3H); 1.45-1.75 (m, 4H); 1.604 (s, 6H); 2.352 (s, 6H); 3.132-3.32 (multiplets, 15H); 3.67 (multiplet, 4H); 4.025 (quadruplet, 2H); 4.05 (sb, 1H); 4.75 (sb, 1H ); 6.736 (s, 1H); 6.968 (s, 1H); 7.020(s, 2H); 7.965 (s, 1H); 8.217 (s, 1H). MS-ESI: 746 [M+H]$^+$ The starting material was prepared as follows

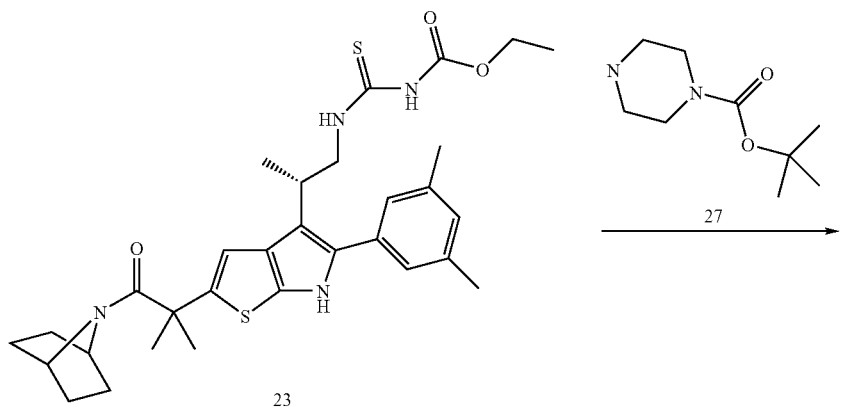

23

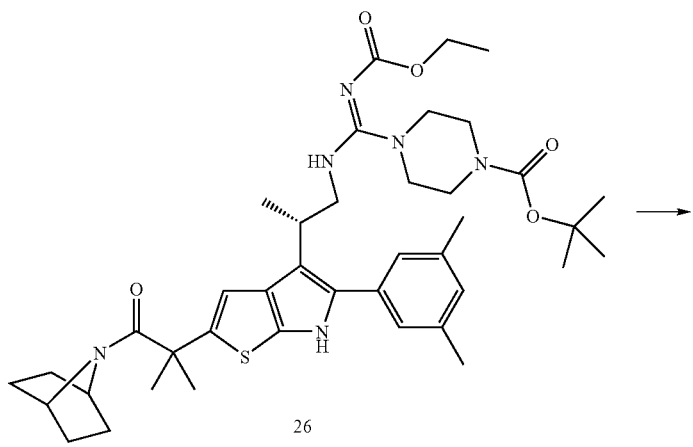

26

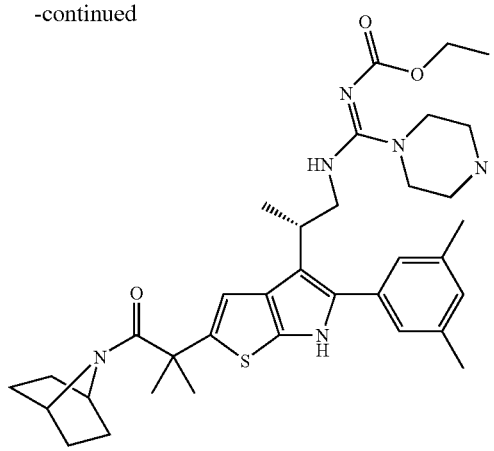

24

To a solution of 23 (0.156 g; 0.27 mmol) in CH$_2$Cl$_2$ (6 ml) at 0° C. was added under argon atmosphere 27 (0.076 g; 0.405 mmol), EDC (0.078 g; 0.405 mmol) and DIEA (0.07 ml; 0.405 mmol). The mixture was stirred at 0° C. for 15 minutes allowed to warm up and stirred for 24 hours at ambient temperature. The reaction mixture was extracted with CH$_2$Cl$_2$. The organic layer was evaporated and the crude material was purified by flash chromatography eluting successively with methylene chloride, methylene chloride/AcOEt 50/50 and 3.5 N NH$_3$ MeOH/AcOEt 5/95 to give 26 as a solid.

Yield: 58% $^1$H NMR (CDCl$_3$) 1.235 (t, 3H); 1.20-1.35 (m, 4H); 1.396 (d, 3H); 1.450 (s, 9H); 1.55-1.75 (m, 4H); 1.598 (s, 6H); 2.352 (s, 6H); 3.131-3.379 (multiplets, 11H); 4.025 (quadruplet, 2H); 4.05 (sb, 1H); 4.75 (sb, 1H); 6.744 (s, 1H); 6.970 (s, 1H); 7.017 (s, 2H); 7.92 (s, 1H); 8.188 (s, 1H).

26 (0.06 g; 0.82 mmol) was dissolved in methylene chloride (0.6 ml) and treated with a solution made of 12N HCl/dioxan 5/25 (1 ml). The mixture stirred under argon atmosphere overnight. After evaporation to dryness, the residue was neutralised and extracted with AcOEt. The organic layer was separated, dried and evaporated to dryness. The residue was triturated with methylene chloride/ether to give 27 triturated in a mixture of MeOH, methylene chloride and ether to give 24 as solid.

Yield: 88% $^1$H RMN (CDCl$_3$) 1.235 (t, 3H); 1.20-1.35 (m, 4H); 1.33 (d, 3H); 1.45-1.75 (m, 4H); 1.62 (s, 6H); 2.35 (s, 6H); 2.85 (multiplet, 4H); 3.26-3.38 (multiplets, 7H); 4.025 (quadruplet, 2H); 4.05 (sb, 1H); 4.75 (sb, 1H); 6.74 (s, 1H); 6.96 (s, 1H); 7.02 (s, 2H); 8.01 (s, 1H); 8.41 (s, 1H); +1 NH.

Example 6

2-(1,1-dimethyl-2-oxo-2-azabicyclo[2.2.1]heptan-7-ylethyl)-4-[1S-methyl-2-(N'-aminocarbonyl-3-pyrid-4-yl-pyrrolin-1-ylcarboximidamido)ethyl]-5-(3,5-dimethylphenyl)-6H-thieno[2,3-b]pyrrole

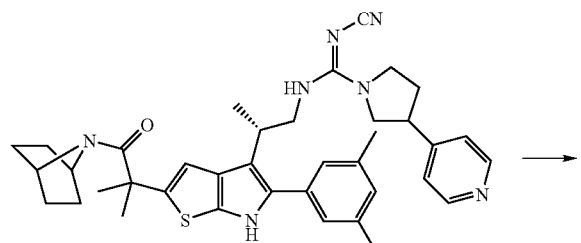

28

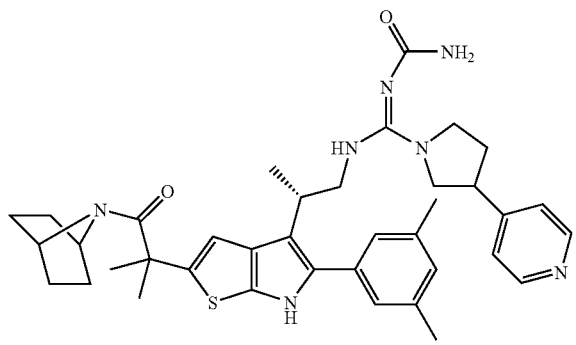

Example 6

To a stirred solution of 28 (0.39 g; 0.603 mmol) in THF (5 ml) at room temperature, was added a 18% (v/v) aqueous solution of HCl. The resulting yellow solution was heated at 80° C. for 4 hours after which HPLC showed no remaining starting material. The reaction mixture was allowed to cool down to room temperature and concentrated on a rotary evaporator. A solution of saturated aqueous brine (5 ml) and saturated aqueous NaHCO$_3$ (5 ml) were added and the resulting oil was extracted with DCM (100 ml). The organic layer was separated, washed with brine (10 ml), dried over magnesium sulfate and concentrated to afford an orange gum. The gum was dissolved in DCM (1 ml) and purified by flash chromatography on silica gel eluting with DCM-MeOH (95:5) to afford the Example 6 (0.067 g).

Yield: 16.8%. $^1$H NMR (CDCl$_3$) (δ ppm) 1.22-1.75 (m, 15H); 1.88-1.94 (m, 1H); 2.15-2.47 (m, 9H); 3.23-3.73(m, 8H); 4.07 (sb, 1H); 4.76 (sb, 1H); 6.74 (m, 1H); 6.97 (m, 1H); 6.98-7.11 (m, 4H); 8.56 (m, 2H). MS-ESI: 666 [M+H]$^+$ The intermediate 24 was prepared using similar chemistry than that used for the preparation of Example 1.0.

Example 7

2-(1,1-dimethyl-2-oxo-2-azabicyclo[2.2.1]heptan-7-ylethyl)-4-[1S-methyl-2-(N'-methylcarbonyl-3-pyrid-4-yl-pyrrolidin-1-ylcarboximidamido)ethyl]-5-(3,5-dimethylphenyl)-6H-thieno[2,3-b]pyrrole

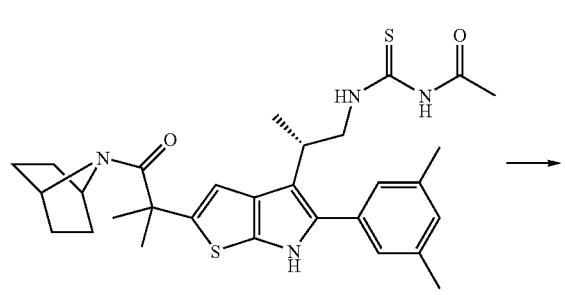

29

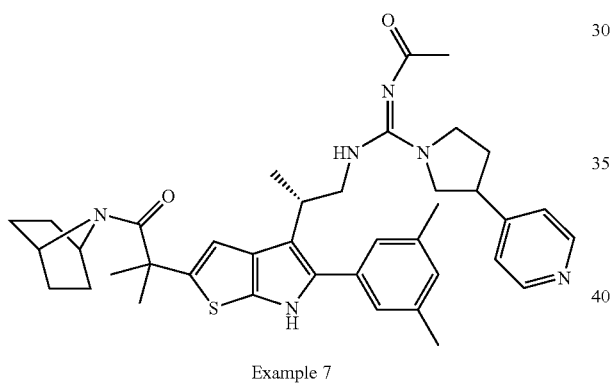

Example 7

To a stirred solution of 29 (0.193 g; 0.351 mmol), DIPEA (0.068 g; 0.527 mmol) and 4-pyrrolidin-3-yl pyridine (0.057 g; 0.386 mmol) in DMF (1 ml) at room temperature, was added solid EDCI (0.074 g; 0.386 mmol). The reaction mixture was heated at 80° C. for 16 hours after which HPLC showed no remaining starting material. The reaction mixture was cooled to room temperature, triturated with water (5 ml) and the resulting solid was collected by filtration, dissolved in DCM (2 ml) and purified by flash chromatography on silica gel eluting with DCM-MeOH (97:3) to afford Example 7 (0.03 g).

Yield: 12%. $^1$H NMR (CDCl$_3$) (δ ppm) 1.22-1.37 (m, 7H); 1.43 (m, 2H); 1.52-1.74(m,8H); 1.88-1.94 (m, 1H); 2.06 (m, 3H); 2.19-2.42 (m, 8H); 3.23-3.41 (m, 5H); 3.57 (m, 2H); 4.07 (sb, 1H); 4.73 (sb, 1H); 6.77 (s, 1H); 6.96 (m, 1H); 7.04-7.11 (m, 4H); 8.27 (s, 1H); 8.53 (m, 2H). MS-ESI: 665 [M+H]$^+$ The intermediate 29 was prepared using similar chemistry than that described for the preparation of intermediate 19.

Example 8

2-(1,1-dimethyl-2-oxo-2-azabicyclo[2.2.1]heptan-7-ylethyl)-4-[1S-methyl-2-(N'-hydroxy-3-pyrid-4-yl-pyrrolidin-1-ylcarboximidamido)ethyl]-5-(3,5-dimethylphenyl)-6H-thieno[2,3-b]pyrrole

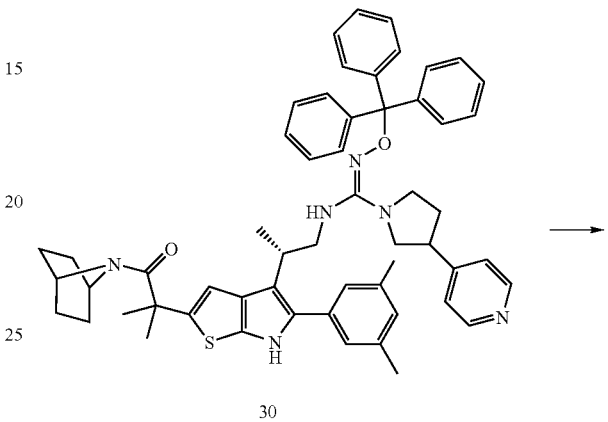

30

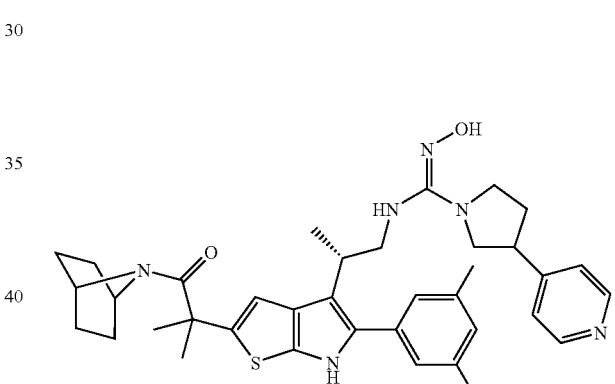

Example 8

To a stirred solution of 30 (0.152 g; 0.173 mmol) in diethyl ether (5 ml) at 0° C., were added MeOH (1 ml) and a 4.0M solution of HCl in 1,4-dioxane (5 ml). The solvent was evaporated to dryness and the residue was suspended in toluene and evaporated to dryness again and further dried under high vacuum. The resulting white foam was triturated with diethyl ether (20 ml) and the resulting white solid collected by filtration, washed with diethyl ether (2×5 ml) and dried to a constant weight to afford Example 8.HCl (0.106 g) as a white solid.

Yield: 85.4%. $^1$H NMR (DMSO-d$_6$) (δ ppm) 1.32 (m, 7H); 1.52 (m, 10H); 1.84-2.04 (m, 4H); 2.25-2.32 (m, 6H); 3.23-3.72 (m, 8H); 4.03 (sb, 1H); 4.45 (sb, 1H); 6.84-7.93 (m, 2H); 7.05 (m, 2H); 7.35 (m, 1H); 7.53 (m, 1H); 7.66 (m, 1H); 7.74 (m, 1H); 8.79 (m, 2H); 10.11-10.19 (m, 1H); 10.55-10.63 (m, 1H); 11.38 (m, 1H). MS-ESI: 639 [M+]$^+$ The intermediate 30 was prepared as follows:

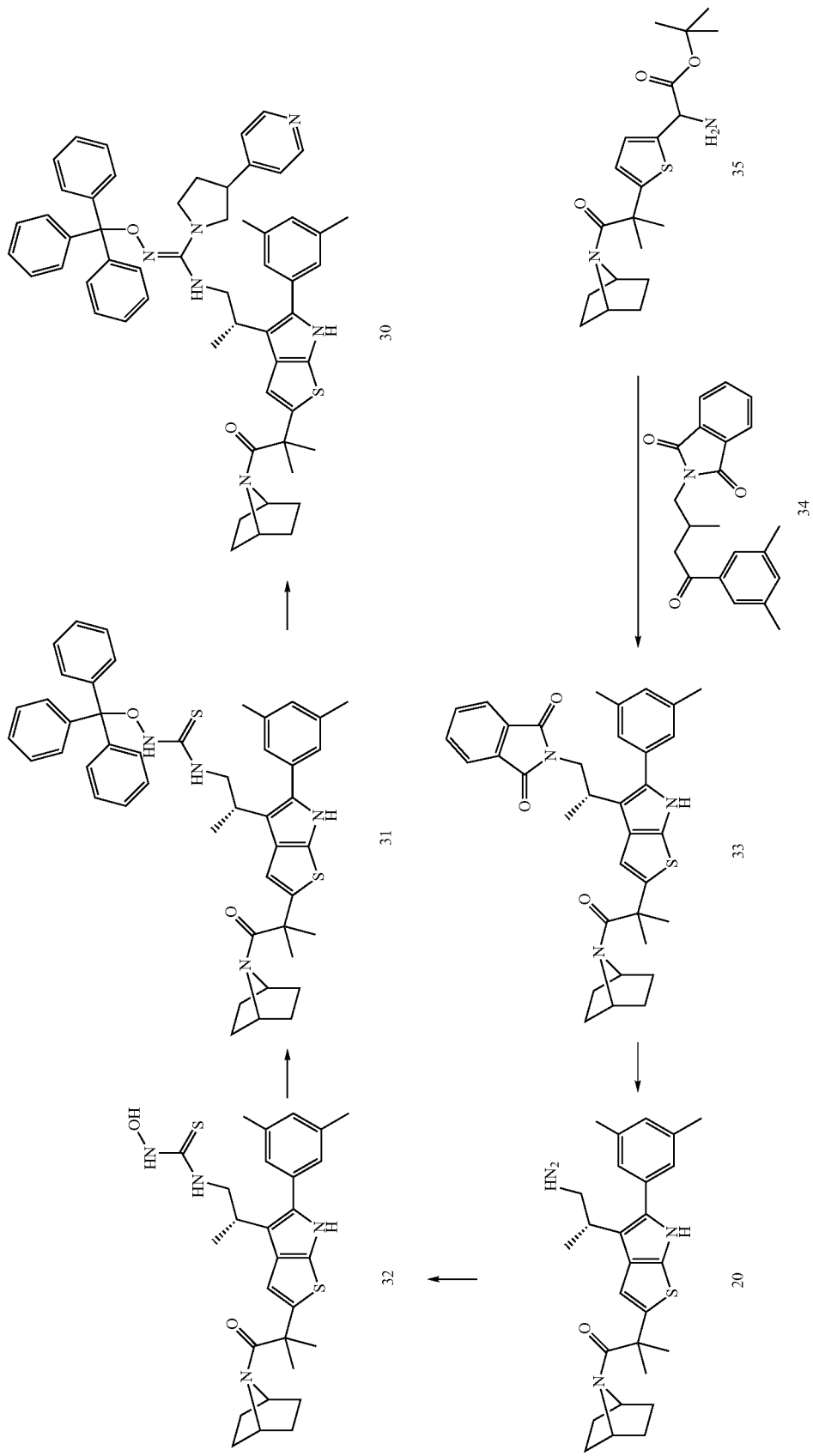

The intermediate 35 was prepared using similar chemistry to that used for the preparation of 9.

To a stirred suspension of 35 (17 g; 45.0 mmol) and 34 (22.5 g; 67.0 mmol) in 2-butanol (50 ml) was added a 4M solution of HCl in 1,4-dioxane (22.5 ml; 90.0 mmol). The resulting thick suspension was heated at 90° C. for 1 hour after which HPLC showed no remaining starting material. The resulting dark brown solution was evaporated to dryness on a rotary evaporator and the residue was dissolved in DCM and purified by flash chromatography on silica gel eluting with ethyl acetate-petroleum ether 40/60 (10:90 to 50/50) to afford 33 (16 g) as a white solid.

Yield: 54% $^1$H NMR (CDCl$_3$) (δ ppm) 1.26-1.40 (m, 7H); 1.57 (s, 6H); 1.63-1.83 (m, 4H); 2.32 (s, 6H); 3.66 (m, 1H); 3.87 (m, 2H); 4.20 (sb, 1H); 4.75 (sb, 1H); 6.86 (s, 1H); 6.92(s, 1H); 6.98 (s, 2H); 7.67 (m, 2H); 7.74 (m, 2H); 8.03 (s, 1H). MS-ESI: 580 [M+H]$^+$ To a stirred suspension of 33 (14 g; 24.0 mmol) in ethanol (300 ml) at room temperature, was added neat hydrazine monohydrate (12 ml; 240 mmol). The reaction mixture was stirred at room temperature for 16 hours after which HPLC showed no remaining starting material. The resulting precipitate was collected by filtration, washed with ethanol (2×20 ml) and the filtrate was evaporated to dryness on a rotary evaporator and dried to a constant weight under high vacuum to afford 20 (10.9 g) as a yellow foam which was used without further purification.

Yield: 100% MS-ESI: 450 [M+H]$^+$ $^1$H NMR (CDCl$_3$) (δ ppm) 1.27-1.36 (m, 7H); 1.43-1.53 (m, 10H); 2.34 (s, 6H); 3.06 (m, 1H); 3.23 (m, 1H); 3.28 (m, 1H); 4.10 (sb, 1H); 4.50 (sb, 1H); 6.87 (s, 1H); 6.96 (s, 1H); 7.07 (s, 2H).

To a stirred solution of 1,1'-thiocarbonyldiimidazole (0.08 g; 0.45 mmol) in MeCN (5 ml) at 0° C., was added a solution of 20 (0.20 g; 0.45 mmol) and DIPEA (0.058 g; 0.45 mmol) in DCM (5 ml). The resulting solution was stirred at room temperature for 1 hour after which HPLC showed no remaining starting material. A 50% (v/v) solution of hydroxylamine in water (0.297 g; 9.00 mmol) was added and the resulting solution was stirred at room temperature for 2 hours after which HPLC showed no remaining starting material. The reaction mixture was evaporated to dryness and the residue was purified by flash chromatography on silica gel eluting with DCM-MeCN (70:30) to afford 32 (0.160 g) as a beige foam.

Yield: 67.8%. MS-ESI: 525 [M+H]$^+$

To a stirred solution of 32 (0.20 g; 0.38 mmol) and triethylamine (0.058 g; 0.57 mmol) in DCM (10 ml) at room temperature, was added triphenylmethyl chloride (0.117 g; 0.42 mmol). The resulting solution was stirred at room temperature for 1 hour after which HPLC showed no remaining starting material. The solvent was evaporated on a rotary evaporator and the residue was purified by flash chromatography on silica gel eluting with DCM-MeCN (80:20) to afford 31 (0.198 g) as a white foam.

Yield: 68%. MS-ESI: 767 [M+H]$^+$

To a stirred solution of 31 (0.198 g; 0.26 mmol), DIPEA (0.050 g; 0.39 mmol) and 4-pyrrolidin-3-yl pyridine (0.039 g; 0.26 mmol) in DCM (2 ml) at room temperature, was added solid EDCI (0.075 g; 0.39 mmol). The reaction mixture was stirred at room temperature for 16 hours after which HPLC showed no remaining starting material. The reaction mixture was purified by flash chromatography on silica gel eluting with DCM-MeCN (90:10) to afford 30 (0.192 g) as a pale yellow foam.

Yield: 83.8%. MS-ESI: 881 [M+H]$^+$

Example 9

2-(1,1-dimethyl-2-oxo-2-azabicyclo[2.2.1]heptan-7-ylethyl)-4-[1S-methyl-2-(N'-methoxycarbonyl-3-pyrid-4-yl-pyrrolidin-1-ylcarboximidamido)ethyl]-5-(3,5-dimethylphenyl)-6H-thieno[2,3-b]pyrrole

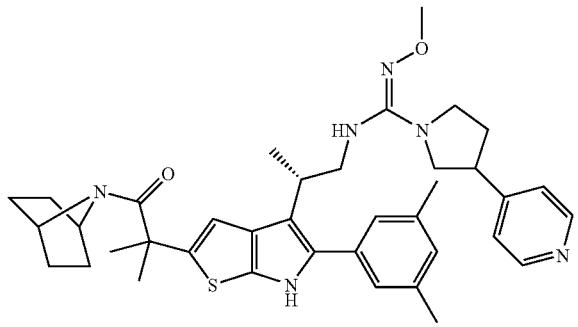

Example 9

Example 9 was prepared using similar chemistry to that described for example 8.

Yield: 52%. $^1$H NMR (CDCl$_3$) (δ ppm) 1.22-1.43 (m, 7H); 1.52-1.73 (m, 10H); 1.79-1.92 (m, 2H); 2.25 (m, 2H); 2.36 (s, 6H); 3.23-3.28 (m, 6H); 3.46 (m, 3H); 4.03 (sb, 1H); 4.75 (sb, 1H); 6.74 (s, 1H); 6.96 (s, 1H); 7.07 (s, 2H); 7.12 (d, 1H); 7.16 (d, 1H); 8.15 (s, 1H); 8.53 (m, 2H). MS-ESI: 653 [M+H]$^+$ Therapeutic Uses Compounds of Formula (I) are provided as medicaments for antagonising gonadotropin releasing hormone (GnRH) activity in a patient, eg, in men and/or women. To this end, a compound of Formula (I) can be provided as part of a pharmaceutical formulation which also includes a pharmaceutically acceptable diluent or carrier (eg, water). The formulation may be in the form of tablets, capsules, granules, powders, syrups, emulsions (eg, lipid emulsions), suppositories, ointments, creams, drops, suspensions (eg, aqueous or oily suspensions) or solutions (eg, aqueous or oily solutions). If desired, the formulation may include one or more additional substances independently selected from stabilising agents, wetting agents, emulsifying agents, buffers, lactose, sialic acid, magnesium stearate, terra alba, sucrose, corn starch, talc, gelatin, agar, pectin, peanut oil, olive oil, cacao butter and ethylene glycol.

The compound is preferably orally administered to a patient, but other routes of administration are possible, such as parenteral or rectal administration. For intravenous, subcutaneous or intramuscular administration, the patient may receive a daily dose of 0.1 mgkg$^{-1}$ to 30 mgkg$^{-1}$ (preferably, 5 mgkg$^{-1}$ to 20 mgkg$^{-1}$) of the compound, the compound being administered 1 to 4 times per day. The intravenous, subcutaneous and intramuscular dose may be given by means of a bolus injection. Alternatively, the intravenous dose may be given by continuous infusion over a period of time. Alternatively, the patient may receive a daily oral dose which is approximately equivalent to the daily parenteral dose, the composition being administered 1 to 4 times per day. A suitable pharmaceutical formulation is one suitable for oral administration in unit dosage form, for example as a tablet or capsule, which contains between 10 mg and 1 g (preferably, 100 mg and 1 g) of the compound of the invention.

Buffers, pharmaceutically acceptable co-solvents (eg, polyethylene glycol, propylene glycol, glycerol or EtOH) or complexing agents such as hydroxy-propyl β cyclodextrin may be used to aid formulation.

One aspect of the invention relates to the use of compounds according to the invention for reducing the secretion of LH and/or FSH by the pituitary gland of a patient. In this respect, the reduction may be by way of a reduction in biosynthesis of the LH and FSH and/or a reduction in the release of LH and FSH by the pituitary gland. Thus, compounds according to the invention can be used for therapeutically treating and/or preventing a sex hormone related condition in the patient. By "preventing" we mean reducing the patient's risk of contracting the condition. By "treating" we mean eradicating the condition or reducing its severity in the patient. Examples of sex hormone related conditions are: a sex hormone dependent cancer, benign prostatic hypertrophy, myoma of the uterus, endometriosis, polycystic ovarian disease, uterine fibroids, prostatauxe, myoma uteri, hirsutism and precocious puberty. Examples of sex hormone dependent cancers are: prostatic cancer, uterine cancer, breast cancer and pituitary gonadotrophe adenoma.

The compounds of the invention may be used in combination with other drugs and therapies used to treat/prevent sex-hormone related conditions.

If formulated as a fixed dose such combination products employ the compounds of this invention within the dosage range described herein and the other pharmaceutically-active agent within its approved dosage range. Sequential use is contemplated when a combination formulation is inappropriate.

In the field of medical oncology examples of such combinations include combinations with the following categories of therapeutic agent:

i) anti-angiogenic agents (for example linomide, inhibitors of integrin αvβ3 function, angiostatin, endostatin, razoxin, thalidomide) and including vascular endothelial growth factor (VEGF) receptor tyrosine kinase inhibitors (RTKIs) (for example those described in international patent applications publication nos. WO-97/22596, WO-97/30035, WO-97/32856 and WO-98/13354, the entire disclosure of which documents is incorporated herein by reference);

ii) cytostatic agents such as anti-oestrogens (for example tamoxifen, toremifene, raloxifene, droloxifene, iodoxyfene), progestogens (for example megestrol acetate), aromatase inhibitors (for example anastrozole, letrozole, vorazole, exemestane), anti-progestogens, anti-androgens (for example flutamide, nilutamide, bicalutamide, cyproterone acetate), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example epidermal growth factor (EGF), platelet derived growth factor and hepatocyte growth factor such inhibitors include growth factor antibodies, growth factor receptor antibodies, tyrosine kinase inhibitors and serine/threonine kinase inhibitors);

iii) biological response modifiers (for example interferon);

iv) antibodies (for example edrecolomab); and v) anti-proliferative/anti-neoplastic drugs and combinations thereof, as used in medical oncology, such as anti-metabolites (for example anti-folates like methotrexate, fluoropyrimidines like 5-fluorouracil, purine and adenosine analogues, cytosine arabinoside); anti-tumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); anti-mitotic agents (for example vinca alkaloids like vincristine and taxoids like taxol, taxotere); enzymes (for example asparaginase); thymidylate synthase inhibitors (for example raltitrexed); topoisomerase inhibitors (for example epipodophyllotoxins like etoposide and teniposide, amsacrine, topotecan, irinotecan).

The compounds of the invention may also be used in combination with surgery or radiotherapy.

Assays

The ability of compounds according to the invention to act as antagonists of GnRH can be determined using the following in vitro assays.

Binding Assay Using Rat Pituitary GnRH Receptor

The assay is performed as follows:

1. Incubate crude plasma membranes prepared from rat pituitary tissues in a Tris.HCl buffer (pH. 7.5, 50 mM) containing bovine serum albumin (0.1%), [I-125]D-t-Bu-Ser6-Pro9-ethyl amide-GnRH, and the test compound. Incubation is at 4° C. for 90 minutes to 2 hours.
2. Rapidly filter and repeatedly wash through a glass fibre filter.
3. Determine the radioactivity of membrane bound radioligands using a gamma counter.

From this data, the $IC_{50}$ of the test compound can be determined as the concentration of the compound required to inhibit radio-ligand binding to GnRH receptors by 50%. Compounds according to the present invention have activity at a concentration from 1 nM to 5 μM.

Binding Assay Using Human GnRH Receptor

Crude membranes prepared from CHO cells expressing human GnRH receptors are sources for the GnRH receptor. The binding activity of compounds according to the invention can be determined as an $IC_{50}$ which is the compound concentration required to inhibit the specific binding of [$^{125}$I]buserelin to GnRH receptors by 50%. [$^{125}$I]Buserelin (a peptide GnRH analogue) is used here as a radiolabelled ligand of the receptor.

Assay to Determine Inhibition of LH Release

The LH release assay can be used to demonstrate antagonist activity of compounds, as demonstrated by a reduction in GnRH-induced LH release.

Preparation of Pituitary Glands

Pituitary glands obtained from rats are prepared as follows. Suitable rats are Wistar male rats (150-200 g) which have been maintained at a constant temperature (eg, 25° C.) on a 12 hour light/12 hour dark cycle. The rats are sacrificed by decapitation before the pituitary glands are aseptically removed to tube containing Hank's Balanced Salt Solution (HBSS). The glands are further processed by:—

1. Centrifugation at 250×g for 5 minutes;
2. Aspiration of the HBSS solution;
3. Transfer of the glands to a petri dish before mincing with a scalpel;

4. Transfer of the minced tissue to a centrifuge tube by suspending the tissue three successive times in 10 ml aliquots of HBSS containing 0.2% collagenase and 0.2% hyaluronidase;
5. Cell dispersion by gentle stirring of the tissue suspension while the tube is kept in a water bath at 37° C.;
6. Aspiration 20 to 30 times using a pipette, undigested pituitary fragments being allowed to settle for 3 to 5 minutes;
7. Aspiration of the suspended cells followed by centrifugation at 1200×g for 5 minutes;
8. Re-suspension of the cells in culture medium of DMEM containing 0.37% $NaHCO_3$, 10% horse serum, 2.5% foetal bovine serum, 1% non essential amino acids, 1% glutamine and 0.1% gentamycin;
9. Treatment of the undigested pituitary fragments 3 times with 30 ml aliquots of the collagenase and hyaluronidase;
10. Pooling of the cell suspensions and dilution to a concentration of $3 \times 10^5$ cells/ml;
11. Placing of 1.0 ml of this suspension in each of a 24 well tray, with the cells being maintained in a humidified 5% $CO_2$/95% air atmosphere at 37° C. for 3 to 4 days Testing of Compounds The test compound is dissolved in DMSO to a final concentration of 0.5% in the incubation medium.

1.5 hours prior to the assay, the cells are washed three times with DMEM containing 0.37% $NaHCO_3$, 10% horse serum, 2.5% foetal bovine serum, 1% non essential amino acids (100×), 1% glutamine (100×), 1% penicillin/streptomycin (10,000 units of each per ml) and 25 mM HEPES at pH 7.4. Immediately prior to the assay, the cells are again washed twice in this medium.

Following this, 1ml of fresh medium containing the test compound and 2 nM GnRH is added to two wells. For other test compounds (where it is desired to test more than one compound), these are added to other respective duplicate wells. Incubation is then carried out at 37° C. for three hours.

Following incubation, each well is analysed by removing the medium from the well and centrifuging the medium at 2000×g for 15 minutes to remove any cellular material. The supernatant is removed and assayed for LH content using a double antibody radio-immuno assay. Comparison with a suitable control (no test compound) is used to determine whether the test compound reduces LH release. Compounds according to the present invention have activity at a concentration from 1 nM to 5 μM.

The invention claimed is:

1. A compound of Formula (I),

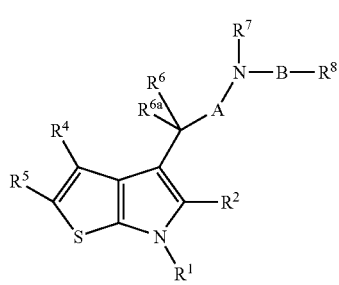

Formula (I)

wherein
A represents a direct bond or optionally substituted $C_{1-5}$alkylene;

B is a group of Formula (II):

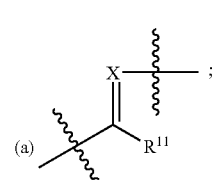

Formula (II)

wherein at position (a) Formula (II) is attached to the nitrogen atom and the group X is attached to $R^8$;

$R^1$ represents hydrogen; optionally substituted $C_{1-8}$alkyl; or $(CH_2)_b$—$R^a$, wherein $R^a$ represents $C_{3-8}$cycloalkyl and b is zero or an integer from 1 to 6;

$R^2$ represents an optionally substituted mono- or bi-cyclic aromatic ring structure wherein the optional substituents are selected from cyano, $NR^3R^{3a}$, optionally substituted $C_{1-8}$alkyl, optionally substituted $C_{1-8}$alkoxy or halo;

$R^3$ and $R^{3a}$ are independently selected from hydrogen; optionally substituted $C_{1-8}$alkyl and optionally substituted aryl;

$R^4$ is hydrogen;

$R^5$ is selected from an optionally substituted 3- to 8-membered heterocyclic ring containing from 1 to 4 heteroatoms independently selected from O, N and S; or a group of formula III-a; III-b; III-c; III-d; III-e; III-f, III-g, III-h, III-i, III-j, III-k or III-l;

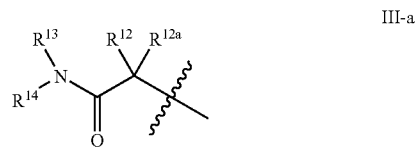

III-a

III-b

III-c

III-d

III-e

III-f

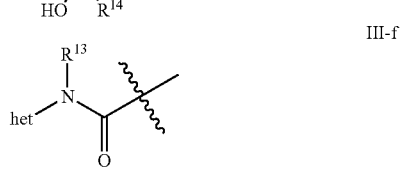

-continued

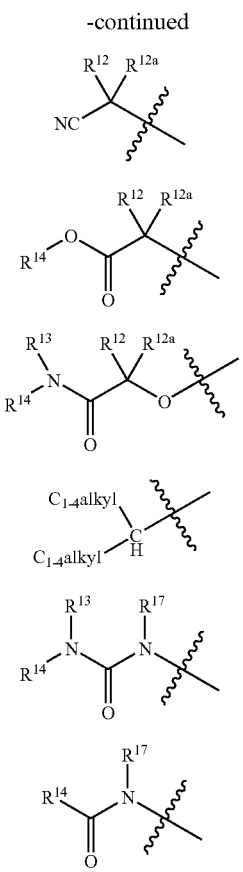

wherein het represents an optionally substituted 3- to 8-membered heterocyclic ring containing from 1 to 4 heteroatoms independently selected from O, N and S;

$R^6$ and $R^{6a}$, are independently selected from hydrogen and optionally substituted $C_{1-8}$alkyl; or $R^6$ and $R^{6a}$ together represent carbonyl;

$R^7$ represents hydrogen or optionally substituted $C_{1-8}$alkyl; or

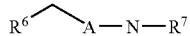

together form an optionally substituted 3- to 8-membered heterocyclic ring containing from 1 to 3 further heteroatoms independently selected from O, N and S, and $R^{6a}$ represents hydrogen and optionally substituted $C_{1-8}$alkyl;

X and $R^8$ are selected from:
(i) X represents N and $R^8$ is selected from:
cyano, hydrogen, hydroxy, —O—$R^b$, —C(O)—$R^b$, —NR$^b$R$^c$—C(O)O—$R^b$, —CONR$^b$R$^c$ or NH—C(O)—$R^b$, where $R^b$ and $R^c$ are independently selected from hydrogen and $C_{1-4}$alkyl optionally substituted with hydroxy, amino, N—$C_{1-4}$alkylamino, N,N-di-$C_{1-4}$alkylamino, HO—$C_{2-4}$alkyl-NH— or HO—$C_{2-4}$alkyl-N($C_{1-4}$alkyl)-;
(ii) X represents CH and $R^8$ represents $NO_2$; and
(iii) =X—$R^8$ represents =O;

$R^{11}$ is a group of the formula: N($R^9R^{10}$) wherein $R^9$ represents hydrogen, optionally substituted aryl, an optionally substituted 3- to 10 membered heterocyclic ring or optionally-substituted $C_{1-8}$alkyl and $R^{10}$ represents hydrogen or optionally substituted $C_{1-8}$alkyl; or the structure N($R^9R^{10}$) represents an optionally-substituted 3- to 10 membered heterocyclic ring optionally containing from 1 to 3 further heteroatoms independently selected from O, N and S;

$R^{12}$ and $R^{12a}$ are independently selected from hydrogen or optionally substituted $C_{1-8}$alkyl; or $R^{12}$ and $R^{12a}$ together with the carbon to which they are attached form an optionally substituted 3 to 7-membered cycloalkyl ring;

$R^{13}$ and $R^{14}$ are selected from:
(i) $R^{13}$ is selected from hydrogen; optionally substituted $C_{1-8}$alkyl; optionally substituted aryl; —$R^d$—Ar, where $R^d$ represents $C_{1-8}$alkylene and Ar represents optionally substituted aryl; and optionally substituted 3- to 8-membered heterocyclic ring optionally containing from 1 to 3 further heteroatoms independently selected from O, N and S; and $R^{14}$ is selected from hydrogen; optionally substituted $C_{1-8}$alkyl and optionally substituted aryl;
(ii) where $R^5$ represents a group of formula III-a, III-b, III-i or III-k, then the group N$R^{13}$(—$R^{14}$) represents an optionally substituted 3- to 8-membered heterocyclic ring optionally containing from 1 to 3 further heteroatoms independently selected from O, N and S; or
(iii) where $R^5$ represents structure III-e, then the group

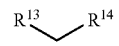

represents an optionally substituted 3- to 8-membered heterocyclic ring optionally containing from 1 to 4 heteroatoms independently selected from O, N and S;

$R^{17}$ is selected from: hydrogen and $C_{1-4}$alkyl;
or a salt, pro-drug or solvate thereof.

2. A compound according to claim 1 wherein $R^9$ represents hydrogen, optionally substituted aryl, an optionally substituted 3- to 10 membered heterocyclic ring or optionally-substituted $C_{1-8}$alkyl and $R^{10}$ represents hydrogen or optionally substituted $C_{1-8}$alkyl wherein the optional substituents on aryl, the heterocyclic ring and $C_{1-8}$alkyl are selected from: hydroxy, amino, nitro, cyano, optionally-substituted aryl, optionally substituted 3- to 8-membered heterocyclyl containing from 1 to 4 heteroatoms independently selected from O, N and S, —O—$R^b$, C(O)NR$^b$R$^c$, —NR$^b$R$^c$, —NR$^c$C(O)—$R^b$, —C(O)NR$^b$R$^c$, —NR$^c$S(O$_{0-2}$)$R^b$, —S(O$_{0-2}$)$R^b$, wherein $R^b$ and $R^c$ are as defined in claim 1.

3. A compound according to claim 2 wherein $R^9$ is a $C_{1-6}$alkyl group substituted by pyridyl, thienyl, piperidinyl, imidazolyl, triazolyl, thiazolyl, pyrrolidinyl, piperazinyl, morpholinyl, imidazolinyl, benztriazolyl, benzimidazolyl, pyrimidinyl, pyrazinyl, pyridazinyl, oxazolyl, furanyl, pyrrolyl, 1,3-dioxolanyl or 2-azetinyl, each of which is optionally substituted as defined in claim 2.

4. A compound according to claim 1 wherein the structure N($R^9R^{10}$) represents an optionally-substituted 3- to 10 membered heterocyclic ring optionally containing from 1 to 3 further heteroatoms independently selected from O, N and S.

5. A compound according to claim 4 wherein the 3- to 10 membered heterocyclic ring is optionally substituted by one of more groups selected from $R^{15}$ wherein $R^{15}$ represents the group $R^{15a}$-Z- wherein $R^{15a}$ is selected from optionally substituted aryl, an optionally substituted 3- to 10 membered heterocyclic ring or optionally substituted $C_{1-4}$alkyl and Z is selected from a a direct bond, —$(CH_2)_{s1}$—, —$(CH_2)_{s1}$—O—$(CH_2)_{s2}$—, —$(CH_2)_{s1}$—C(O)—$(CH_2)_{s2}$—, —$(CH_2)_{s1}$—S(O$_n$)—$(CH_2)_{s2}$—, —$(CH_2)_{s1}$—N(R$^{18}$)—$(CH_2)_{s2}$—, —$(CH_2)_{s1}$—C(O)N(R$^{18}$)—$(CH_2)_{s2}$—, —$(CH_2)_{s1}$—N(R$^{18}$)C(O)—$(CH_2)_{s2}$—, —$(CH_2)_{s1}$—N(R$^{18}$)C(O)N(R$^{18}$)—$(CH_2)_{s2}$—, —$(CH_2)_{s1}$—OC(O)—$(CH_2)_{s2}$—, —$(CH_2)_{s1}$—C(O)O—$(CH_2)_{s2}$—, —$(CH_2)_{s1}$—N(R$^{18}$)C(O)O—$(CH_2)_{s2}$—, —$(CH_2)_{s1}$—OC(O)N(R$^{18}$)—$(CH_2)_{s2}$—, —$(CH_2)_{s1}$—OS(O$_n$)—$(CH_2)_{s2}$—, or —$(CH_2)_{s1}$—S(O$_n$)—O—$(CH_2)_{s2}$—, —$(CH_2)_{s1}$—S(O)$_2$N(R$^{18}$)—$(CH_2)_{s2}$—, —$(CH_2)_{s1}$—N(R$^{18}$)S(O)$_2$—$(CH_2)_{s2}$—; wherein the —$(CH_2)_{s1}$— and —$(CH_2)_{s2}$— groups are independently optionally substituted by hydroxy or $C_{1-4}$alkyl and s1 and s2 are independently an integer from 0 to 2, wherein s1+s2 is less than or equal to 2 and $R^{18}$ is selected from hydrogen or $C_{1-4}$alkyl;

wherein the optional substituents on aryl, a heterocyclic ring or $C_{1-4}$alkyl are selected from: hydroxy, amino, nitro, cyano, optionally-substituted aryl, optionally substituted 3- to 8-membered heterocyclyl containing from 1 to 4 heteroatoms independently selected from O, N and S, —O—R$^g$, —C(O)—R$^g$, —C(O)NR$^g$R$^h$, —NR$^g$R$^h$, —NR$^h$C(O)—R$^g$, —C(O)NR$^g$R$^h$, —NR$^h$S(O$_{0-2}$)R$^g$, —S(O$_{0-2}$)R$^g$, wherein R$^g$ and R$^g$ are independently selected from: heterocyclyl, hydrogen and $C_{1-4}$alkyl optionally substituted with hydroxy, amino, N—$C_{1-4}$alkylamino, N,N-di-$C_{1-4}$alkylamino, HO—$C_{2-4}$ alkyl-NH— or HO—$C_{2-4}$alkyl-N($C_{1-4}$alkyl)-.

6. A compound according to claim 5, wherein Z is selected from a direct bond or carbonyl.

7. A compound according to claim 1 wherein $R^5$ is selected from a group of formula III-a, III-g, III-h, III-i or III-j:

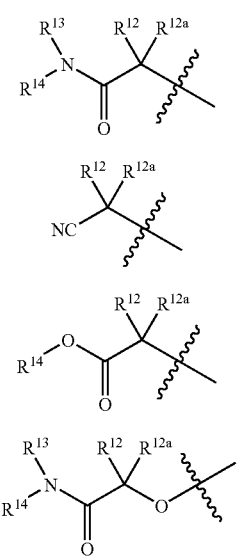

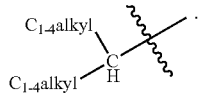

8. A compound according to claim 1 wherein:
(a) X represents N and $R^8$ represents cyano or —C(O)O—R$^b$; wherein R$^b$ is as defined in claim 1, or
(b) X represents N and $R^8$ represents hydrogen.

9. A compound according to claim 1 preceding claims wherein $R^2$ is selected from an optionally substituted monocyclic aromatic ring structure wherein the optional substituents are selected from cyano, NR$^e$R$^f$, optionally substituted $C_{1-8}$alkyl, optionally substituted $C_{1-8}$alkoxy or halo wherein R$^e$ and R$^f$ are independently selected from hydrogen, $C_{1-6}$alkyl or aryl.

10. A compound according to claim 1 preceding claims wherein $R^1$ is hydrogen.

11. A compound selected from:

2-(1,1-dimethyl-2-oxo-2-azabicyclo[2.2.1]heptan-7-yl-ethyl)-4-[1S-methyl-2-(N'-isopropoxycarbonyl-3-pyrid-4-yl-pyrrolidin-1-ylcarboximidamido)ethyl]-5-(3,5-dimethylphenyl)-6H-thieno[2,3-b]pyrrole;

2-(1,1-dimethyl-2-oxo-2-azabicyclo[2.2.1]heptan-7-yl-ethyl)-4-[2-(N'-isopropoxycarbonyl-3-pyrid-4-yl-pyrrolidin-1-ylcarboximidamido)ethyl]-5-(3,5-dimethylphenyl)-6H-thieno[2,3-b]pyrrole;

2-(2-pyrrolidin-1-yl-1,1-dimethyl-2-oxoethyl)-4-[1S-methyl-2-(N'-isopropoxycarbonyl-3-pyrid-4-yl-pyrrolidin-1-ylcarboximidamido)ethyl]-5-(3,5-dimethylphenyl)-6H-thieno[2,3-b]pyrrole;

2-(1,1-dimethyl-2-oxo-2-azabicyclo[2.2.1]heptan-7-yl-ethyl)-4-[1S-methyl-2-(N'-isopropoxycarbonyl-4-tetrahydropyran-4-yl-piperidin-1-ylcarboximidamido)ethyl]-5-(3,5-dimethylphenyl)-6H-thieno[2,3-b]pyrrole;

2-(1,1-dimethyl-2-oxo-2-azabicyclo[2.2.1]heptan-7-yl-ethyl)-4-[1S-methyl-2-(3-pyrid-4-yl-pyrrolidin-1-yl-carbonyl)ethyl]-5-(3,5-dimethylphenyl)-6H-thieno[2,3-b]pyrrole;

2-(1,1-dimethyl-2-oxo-2-azabicyclo[2.2.1]heptan-7-yl-ethyl)-4-[1S-methyl-2-(N'-ethoxycarbonyl-3-pyrid-4-yl-pyrrolidin-1-yl carboximidamido)ethyl]-5-(3,5-dimethylphenyl)-6H-thieno[2,3-b]pyrrole;

or a salt, pro-drug or solvate thereof.

12. A pharmaceutical formulation comprising a compound, or salt, pro-drug or solvate thereof, according to claim 1 and a pharmaceutically acceptable diluent or carrier.

13. A method of antagonising gonadotropin releasing hormone activity, the method comprising administering a compound according to claim 1, or salt, pro-drug or solvate thereof, to a patient.

14. A process of producing a compound, or salt, pro-drug or solvate thereof, according to claim 1, wherein the process comprises a reaction step selected from any one of steps (a) to (f):

(a) Reaction of a compound of formula XXXII as follows

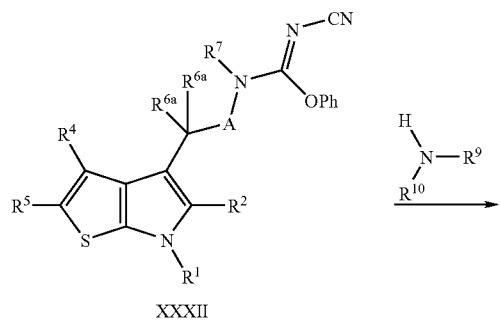

XXXII

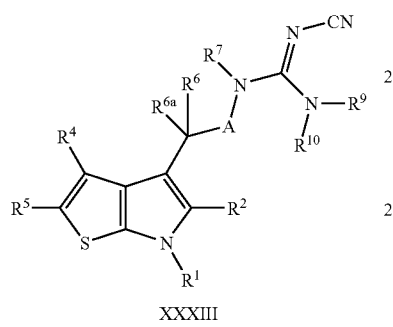

XXXIII (b) Cleavage of the cyano group of a compound of formula XXXIII in the presence of acid to produce a compound of formula XXXIV

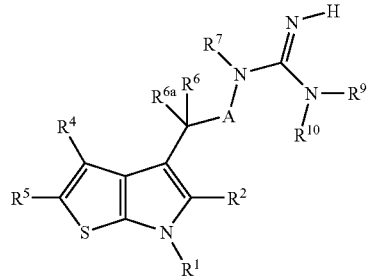

XXXIV (c) Reaction of a compound of formula XXXV as follows

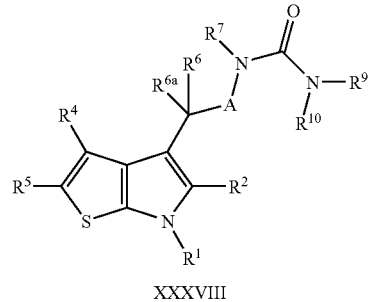

XXXV

-continued

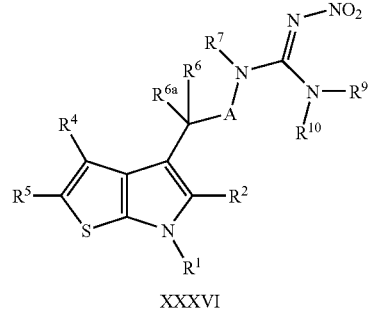

XXXVI (d) Reaction of a compound of formula XXXVII as follows

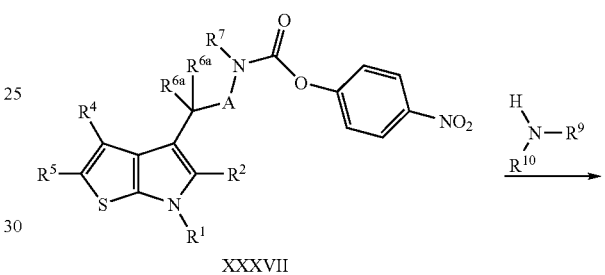

XXXVII

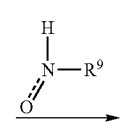

XXXVIII (e) Reaction of a compound of formula XXXIX as follows

XXXIX

-continued
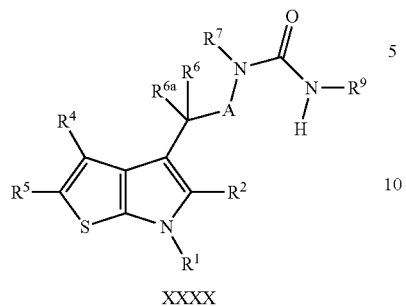
XXXX
(f) Reaction of a compound of formula XXXXI as follows to form a compound wherein X is nitrogen and
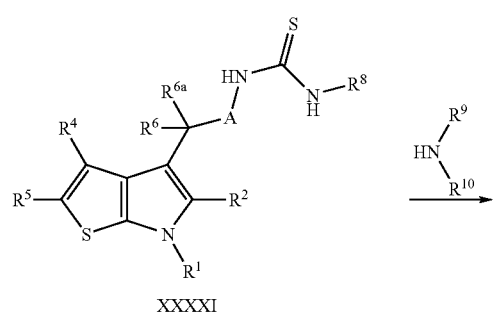
XXXXI
-continued
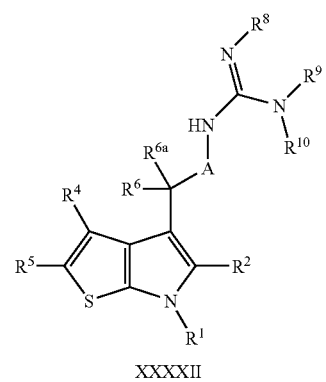
XXXXII
and thereafter if necessary:
i) converting a compound of the Formula (I) into another compound of the Formula (I);
ii) removing any protecting groups;
iii) forming a salt, pro-drug or solvate.
* * * * *